(12) United States Patent
Weizman et al.

(10) Patent No.: US 7,998,167 B2
(45) Date of Patent: Aug. 16, 2011

(54) END EFFECTOR AND METHOD OF MANUFACTURE

(75) Inventors: Patrick A. Weizman, Liberty Township, OH (US); Douglas J. Turner, Cincinnati, OH (US); Richard F. Schwemberger, Cincinnati, OH (US); Stephen W. Evans, West Chester, OH (US); Dean Bruewer, Fairfield, OH (US); Gina M. Szweda, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1051 days.

(21) Appl. No.: 11/404,989

(22) Filed: Apr. 14, 2006

(65) Prior Publication Data

US 2007/0244514 A1    Oct. 18, 2007

(51) Int. Cl.
*A61B 17/00* (2006.01)
(52) U.S. Cl. .................................... 606/207
(58) Field of Classification Search .................. 600/564, 600/104, 141, 142; 606/174, 207, 208, 205, 606/206, 51, 52; 433/159; D24/143; D8/52, D8/54; 81/418, 176.3, 119, 318
See application file for complete search history.

(56) References Cited

U.S. PATENT DOCUMENTS

| | | |
|---|---|---|
| 534,570 A | 2/1895 | Norris |
| 1,515,000 A | 11/1924 | Thompson |
| 2,034,785 A | 3/1936 | Wappler |
| 3,461,708 A | 8/1969 | Pepe |
| 3,521,620 A | 7/1970 | Cook |
| 3,608,539 A | 9/1971 | Miller |
| 3,687,131 A | 8/1972 | Rayport et al. |
| 3,739,784 A | 6/1973 | Itoh |
| 3,791,387 A | 2/1974 | Itoh |
| 3,895,636 A | 7/1975 | Schmidt |
| 3,949,747 A | 4/1976 | Hevesy |
| 3,973,556 A | 8/1976 | Fleischhacker et al. |
| 4,038,987 A | 8/1977 | Komiya |
| 4,043,323 A | 8/1977 | Komiya |
| 4,080,706 A | 3/1978 | Heilman et al. |
| 4,174,715 A | 11/1979 | Hasson |
| 4,427,014 A | 1/1984 | Bel et al. |
| 4,592,341 A | 6/1986 | Omagari et al. |
| 4,597,385 A | 7/1986 | Watson |
| 4,632,110 A | 12/1986 | Sanagi |
| 4,633,871 A | 1/1987 | Shinozuka |
| 4,634,042 A | 1/1987 | Smith |
| 4,646,751 A | 3/1987 | Maslanka |
| 4,653,477 A | 3/1987 | Akui et al. |
| 4,669,471 A | 6/1987 | Hayashi |
| 4,682,599 A | 7/1987 | Konomura |
| 4,715,360 A | 12/1987 | Akui et al. |

(Continued)

FOREIGN PATENT DOCUMENTS

WO    WO 2004/103190 A1    12/2004

*Primary Examiner* — Todd E Manahan
*Assistant Examiner* — Jonathan A Hollm
(74) *Attorney, Agent, or Firm* — Welsh Flexman & Gitler LLC

(57) ABSTRACT

An end effector for use in an endoscopic device including a cup, and a hinge extension formed separately from the cup and connected to the cup. The hinge extension has a pivot for pivotally connecting the end effector to an identical second end effector.

18 Claims, 25 Drawing Sheets

U.S. PATENT DOCUMENTS

| | | |
|---|---|---|
| 4,721,116 A | 1/1988 | Schintgen et al. |
| 4,763,668 A | 8/1988 | Macek et al. |
| 4,763,669 A | 8/1988 | Jaeger |
| 4,815,476 A | 3/1989 | Clossick |
| 4,817,630 A | 4/1989 | Schintgen et al. |
| 4,880,015 A | 11/1989 | Nierman |
| 4,887,612 A | 12/1989 | Esser et al. |
| 4,909,789 A | 3/1990 | Taguchi et al. |
| 4,945,920 A | 8/1990 | Clossick |
| 4,971,067 A | 11/1990 | Bolduc et al. |
| 4,982,727 A | 1/1991 | Sato |
| 4,994,079 A | 2/1991 | Genese et al. |
| 5,052,402 A | 10/1991 | Bencini et al. |
| 5,084,054 A | 1/1992 | Bencini et al. |
| 5,094,247 A | 3/1992 | Hernandez et al. |
| 5,097,728 A | 3/1992 | Cox et al. |
| 5,100,430 A | 3/1992 | Avellanet et al. |
| 5,133,727 A | 7/1992 | Bales et al. |
| 5,133,735 A | 7/1992 | Slater et al. |
| 5,133,736 A | 7/1992 | Bales, Jr. et al. |
| 5,141,519 A | 8/1992 | Smith et al. |
| 5,147,380 A | 9/1992 | Hernandez et al. |
| 5,152,778 A | 10/1992 | Bales, Jr. et al. |
| 5,156,633 A | 10/1992 | Smith |
| 5,170,800 A | 12/1992 | Smith et al. |
| 5,171,256 A | 12/1992 | Smith et al. |
| 5,171,258 A | 12/1992 | Bales et al. |
| 5,172,700 A | 12/1992 | Bencini et al. |
| 5,184,625 A | 2/1993 | Cottone, Jr. et al. |
| 5,192,298 A | 3/1993 | Smith et al. |
| 5,203,785 A | 4/1993 | Slater |
| 5,215,101 A | 6/1993 | Jacobs et al. |
| 5,228,451 A | 7/1993 | Bales et al. |
| 5,238,002 A | 8/1993 | Devlin et al. |
| 5,241,968 A | 9/1993 | Slater |
| 5,250,073 A | 10/1993 | Cottone, Jr. |
| 5,251,638 A | 10/1993 | Cottone, Jr. et al. |
| 5,312,332 A | 5/1994 | Bales et al. |
| 5,324,301 A | 6/1994 | Drucker |
| 5,331,971 A | 7/1994 | Bales et al. |
| 5,352,223 A | 10/1994 | McBrayer et al. |
| 5,360,432 A | 11/1994 | Shturman |
| 5,383,471 A | 1/1995 | Funnell |
| 5,394,885 A | 3/1995 | Francese |
| 5,395,369 A | 3/1995 | McBrayer et al. |
| 5,396,900 A | 3/1995 | Slater et al. |
| 5,419,220 A | 5/1995 | Cox |
| 5,419,339 A | 5/1995 | Palmer |
| 5,431,645 A | 7/1995 | Smith et al. |
| 5,439,478 A | 8/1995 | Palmer |
| 5,454,378 A | 10/1995 | Palmer et al. |
| 5,471,992 A | 12/1995 | Banik et al. |
| 5,476,099 A | 12/1995 | Robinson et al. |
| 5,482,054 A | 1/1996 | Slater et al. |
| 5,490,861 A | 2/1996 | Kratsch et al. |
| 5,491,881 A | 2/1996 | Collins |
| 5,507,296 A | 4/1996 | Bales et al. |
| 5,507,297 A | 4/1996 | Slater et al. |
| 5,535,754 A | 7/1996 | Doherty |
| 5,542,432 A | 8/1996 | Slater et al. |
| 5,549,606 A | 8/1996 | McBrayer et al. |
| 5,553,624 A | 9/1996 | Francese et al. |
| 5,558,100 A | 9/1996 | Cox |
| 5,569,243 A | 10/1996 | Kortenbach et al. |
| 5,569,299 A | 10/1996 | Dill et al. |
| 5,571,129 A | 11/1996 | Porter |
| 5,571,136 A | 11/1996 | Weaver |
| 5,573,008 A | 11/1996 | Robinson et al. |
| 5,578,056 A | 11/1996 | Pauldrach |
| 5,586,990 A | 12/1996 | Hahnen et al. |
| 5,591,202 A | 1/1997 | Slater et al. |
| 5,601,585 A | 2/1997 | Banik et al. |
| 5,613,499 A | 3/1997 | Palmer et al. |
| 5,636,639 A | 6/1997 | Turturro et al. |
| 5,638,827 A | 6/1997 | Palmer et al. |
| 5,640,874 A | 6/1997 | Vecsey |
| 5,643,307 A | 7/1997 | Turkel et al. |
| 5,645,075 A | 7/1997 | Palmer et al. |
| 5,647,115 A | 7/1997 | Slater et al. |
| 5,666,965 A | 9/1997 | Bales et al. |
| 5,667,525 A | 9/1997 | Ishibashi |
| 5,683,385 A | 11/1997 | Kortenbach et al. |
| 5,683,388 A | 11/1997 | Slater |
| 5,683,412 A | 11/1997 | Scarfone |
| 5,697,949 A | 12/1997 | Giurtino et al. |
| 5,700,276 A | 12/1997 | Benecke |
| 5,702,080 A | 12/1997 | Whittier et al. |
| 5,706,824 A | 1/1998 | Whittier |
| 5,707,392 A | 1/1998 | Kortenbach |
| 5,715,832 A | 2/1998 | Koblish et al. |
| 5,716,374 A | 2/1998 | Francese et al. |
| 5,722,421 A | 3/1998 | Francese et al. |
| 5,722,422 A | 3/1998 | Palmer et al. |
| 5,741,285 A | 4/1998 | McBrayer et al. |
| 5,746,216 A | 5/1998 | Turturro et al. |
| 5,746,740 A | 5/1998 | Nicholas |
| 5,762,070 A | 6/1998 | Nagamatsu |
| 5,766,184 A | 6/1998 | Matsuno et al. |
| 5,776,075 A | 7/1998 | Palmer |
| 5,779,646 A | 7/1998 | Koblish et al. |
| 5,779,701 A | 7/1998 | McBrayer et al. |
| 5,782,748 A | 7/1998 | Palmer et al. |
| 5,797,957 A | 8/1998 | Palmer et al. |
| 5,810,744 A | 9/1998 | Chu et al. |
| 5,810,865 A * | 9/1998 | Koscher et al. ............... 606/174 |
| 5,810,876 A | 9/1998 | Kelleher |
| 5,819,738 A | 10/1998 | Slater |
| 5,823,971 A | 10/1998 | Robinson et al. |
| 5,840,043 A | 11/1998 | Palmer et al. |
| 5,840,044 A | 11/1998 | Dassa et al. |
| 5,843,122 A | 12/1998 | Riza |
| 5,846,240 A | 12/1998 | Kortenbach et al. |
| 5,865,724 A | 2/1999 | Palmer et al. |
| 5,871,453 A | 2/1999 | Banik et al. |
| 5,893,846 A | 4/1999 | Bales et al. |
| 5,893,876 A | 4/1999 | Turkel et al. |
| 5,895,361 A | 4/1999 | Turturro |
| 5,897,507 A | 4/1999 | Kortenbach et al. |
| 5,906,630 A | 5/1999 | Anderhub et al. |
| 5,928,163 A | 7/1999 | Roberts et al. |
| 5,951,488 A | 9/1999 | Slater et al. |
| 5,957,863 A | 9/1999 | Koblish et al. |
| 5,961,534 A | 10/1999 | Banik et al. |
| 5,964,717 A | 10/1999 | Gottlieb et al. |
| 5,967,997 A | 10/1999 | Turturro et al. |
| 5,971,940 A | 10/1999 | Baker et al. |
| 5,976,130 A | 11/1999 | McBrayer et al. |
| 6,007,560 A | 12/1999 | Gottlieb et al. |
| 6,019,758 A | 2/2000 | Slater |
| 6,024,708 A | 2/2000 | Bales et al. |
| 6,030,409 A * | 2/2000 | Lang ............................ 606/205 |
| 6,036,656 A | 3/2000 | Slater |
| 6,041,679 A | 3/2000 | Slater et al. |
| 6,063,103 A | 5/2000 | Hashiguchi |
| 6,066,102 A | 5/2000 | Townsend et al. |
| 6,074,408 A | 6/2000 | Freeman |
| 6,083,150 A | 7/2000 | Aznoian et al. |
| 6,090,108 A | 7/2000 | McBrayer et al. |
| 6,096,037 A | 8/2000 | Mulier et al. |
| 6,099,483 A | 8/2000 | Palmer et al. |
| 6,106,543 A | 8/2000 | Esser |
| 6,123,678 A | 9/2000 | Palmer et al. |
| 6,129,683 A | 10/2000 | Sutton et al. |
| 6,139,508 A | 10/2000 | Simpson et al. |
| 6,142,956 A | 11/2000 | Kortenbach et al. |
| 6,142,957 A | 11/2000 | Diamond et al. |
| 6,149,607 A | 11/2000 | Simpson et al. |
| 6,159,162 A | 12/2000 | Kostylev et al. |
| 6,174,292 B1 | 1/2001 | Kortenbach et al. |
| 6,190,399 B1 | 2/2001 | Palmer et al. |
| 6,193,671 B1 | 2/2001 | Turturro et al. |
| 6,193,718 B1 | 2/2001 | Kortenbach et al. |
| 6,261,242 B1 | 7/2001 | Roberts et al. |
| 6,264,617 B1 | 7/2001 | Bales et al. |
| 6,283,924 B1 | 9/2001 | Ouchi |
| 6,293,954 B1 * | 9/2001 | Fogarty et al. ............... 606/151 |
| 6,299,630 B1 * | 10/2001 | Yamamoto .................... 606/205 |

| | | | | | |
|---|---|---|---|---|---|
| 6,331,165 B1 | 12/2001 | Turturro et al. | 6,613,068 B2 | 9/2003 | Ouchi |
| 6,364,879 B1 * | 4/2002 | Chen et al. ............... 606/45 | 6,689,122 B2 | 2/2004 | Yamamoto |
| 6,375,650 B1 | 4/2002 | Ouchi | 6,740,106 B2 | 5/2004 | Kobayashi et al. |
| 6,378,351 B1 | 4/2002 | Ouchi et al. | 6,743,185 B2 | 6/2004 | Weber et al. |
| 6,427,509 B1 | 8/2002 | Ouchi et al. | 6,792,663 B2 | 9/2004 | Krzyzanowski |
| 6,428,539 B1 | 8/2002 | Baxter et al. | 6,964,662 B2 | 11/2005 | Kidooka |
| 6,440,085 B1 | 8/2002 | Krzyzanowski | 2002/0143358 A1 * | 10/2002 | Domingo et al. ............ 606/190 |
| 6,440,130 B1 | 8/2002 | Mulier et al. | 2002/0165580 A1 | 11/2002 | Zwiefel et al. |
| 6,443,952 B1 | 9/2002 | Mulier et al. | 2004/0181169 A1 | 9/2004 | Diamond et al. |
| 6,447,511 B1 | 9/2002 | Slater | 2004/0249371 A1 * | 12/2004 | Dycus et al. .................. 606/32 |
| 6,494,881 B1 | 12/2002 | Bales et al. | 2004/0260198 A1 | 12/2004 | Rothberg et al. |
| 6,514,197 B1 | 2/2003 | Ouchi et al. | 2004/0260337 A1 | 12/2004 | Freed |
| 6,514,269 B2 | 2/2003 | Yamamoto | 2005/0054946 A1 | 3/2005 | Krzyzanowski |
| 6,544,194 B1 | 4/2003 | Kortenbach et al. | 2005/0131312 A1 | 6/2005 | Endara et al. |
| 6,554,850 B1 | 4/2003 | Ouchi et al. | 2005/0235725 A1 | 10/2005 | Krzyzanowski |
| 6,561,988 B1 | 5/2003 | Turturro et al. | 2006/0184198 A1 * | 8/2006 | Bales et al. .................. 606/205 |
| 6,605,104 B2 | 8/2003 | Sato et al. | | | |
| 6,610,060 B2 | 8/2003 | Mulier et al. | * cited by examiner | | |

END EFFECTOR AND METHOD OF MANUFACTURE

BACKGROUND OF THE INVENTION

The present invention generally relates to endoscopic instruments, and more particularly to biopsy forceps and other endoscopic end effectors.

Endoscopic biopsy forceps are a medical instrument used in combination with an endoscope for removing tissue samples from inside a patient's body for analysis. These instruments typically include an elongate flexible member having a biopsy jaw assembly mounted on one end. The jaw assembly includes a clevis holding pivotally mounted jaws adapted for removing tissue for analysis. An actuator comprising an actuator handle and an actuator member extending from the handle to the pivoting jaws of the jaw assembly moves the jaws between an open position in which the ends of the jaws are spaced and a closed position in which the ends of the jaws contact each other to obtain the tissue sample. In addition to biopsy forceps, some aspects of the present invention relate to other types of endoscopic end effectors such as a flexible grasper, a dissector, or scissors.

Biopsy forceps frequently have teeth along the mating edges of the jaws to improve grasping of the tissue. As will be appreciated by those skilled in the art, the teeth extending along each side of the jaw and those extending across the end of the jaw interact differently with the tissue. In the past, these differences in interaction have not been taken into account when selecting tooth profiles for the different portions of the jaw. A fundamental function of biopsy forceps is to pinch tissue in order to tear a sample free. The teeth, particularly those at the end of the jaw, are believed to have a significant impact on sample depth and weight.

Many conventional jaws have been made so that each jaw in the assembly has a different configuration. When a single jaw assembly uses two different jaw configurations, the different jaws must be manufactured, stored and handled during assembly. This situation results in manufacturing inefficiency and a cost increase. In addition, many conventional jaws are cast or molded. Jaws designed to be manufactured using other less expensive processes have the potential for reducing overall assembly cost.

Because the jaw assembly includes a clevis, certain obstacles are presented during assembly. If the clevis and axle pin are inseparably assembled before the jaws are installed, the arms of the clevis must be spread when the jaws are being assembled with the clevis. If the clevis and axle pin are separate, the jaws must be inserted between the clevis arms and aligned with the axle pin. Either process has a potential for increasing assembly cost. Still further, connecting the actuator members to the jaw assembly is difficult to achieve using conventional devises because the clevis blocks clear access to these components.

Once assembled, the jaw assembly has portions (e.g., distal portions) that are susceptible to higher stresses and wear. In order to optimize the jaw, some portions of the jaw can be thicker or made from different materials. Although producing a jaw cup by stamping has economic advantages, conventional jaw assemblies have been unable to take advantage of a stamped jaw cup while having thicker portions or portions made from different materials.

During use, a large jaw size is desired to obtain a large tissue sample. However, when the forceps are being pushed into position, a small jaw size is desirable so that the forceps can travel through smaller radius turns. Using conventional jaw shapes, the jaw size is limited by turning radius.

Among the problems common to known biopsy forceps and end effectors generally is that these instruments are very long and flexible, making packaging, storage and handling difficult. The instruments are frequently coiled when packaged. When the packaging is opened, the instruments can spontaneously uncoil, become unmanageable, potentially falling on the floor, and becoming contaminated or being damaged. Thus, there is a need for a feature that retains these types of instruments in a coiled configuration when unpackaged.

SUMMARY OF THE INVENTION

Briefly, the present invention includes an end effector for use in an endoscopic device comprising a cup, and a hinge extension formed separately from the cup and connected to the cup. The hinge extension has a pivot for pivotally connecting the end effector to an identical second end effector.

In yet another aspect, the invention includes a method of manufacturing an end effector comprising stamping a cup from sheet metal, and attaching a hinge extension to the cup.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
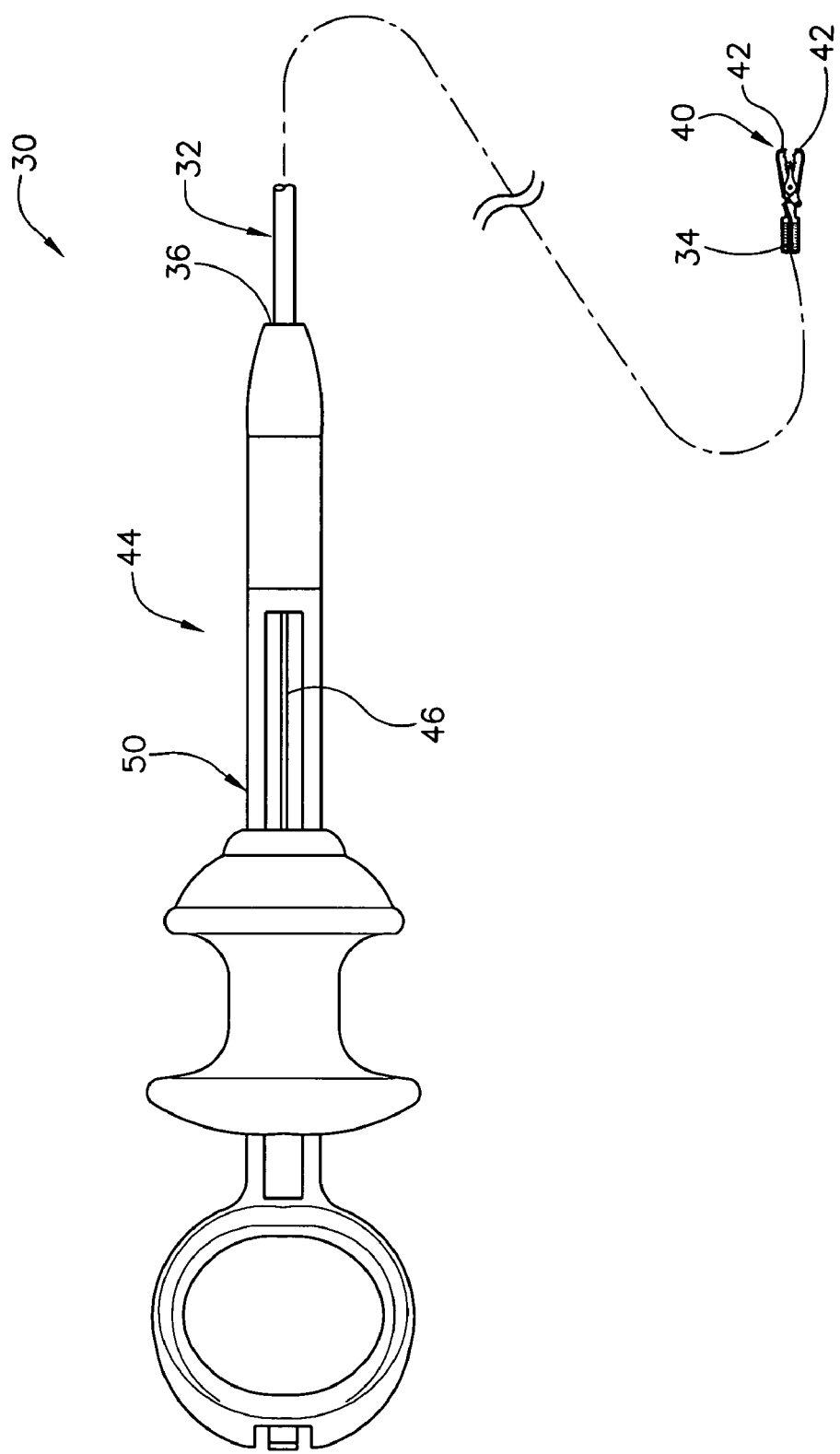
FIG. 1 is a side elevation of biopsy forceps of the present invention.
Figure 6:
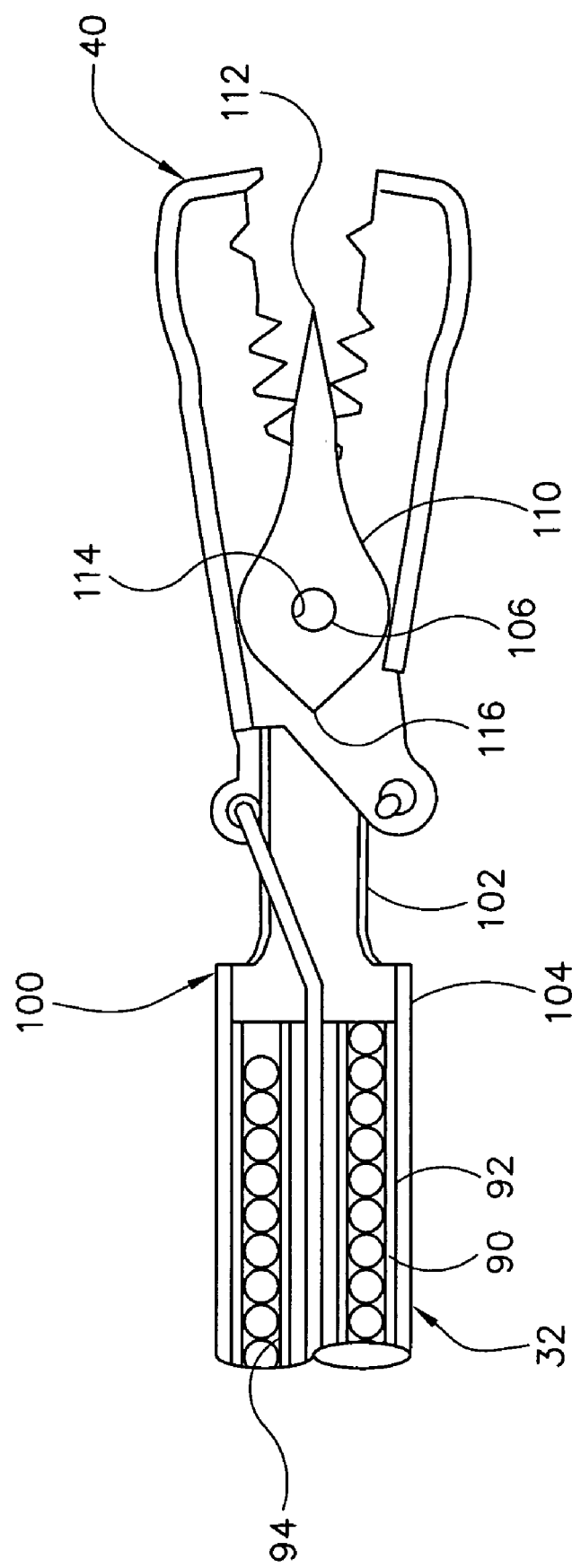
FIG. 6 is a cross section of a jaw assembly of the biopsy forceps showing jaws in an open position.

Referring now to the drawings and in particular to FIG. 1, a surgical instrument of the present invention is designated in its entirety by the reference numeral 30. Although the surgical instrument 30 illustrated in FIG. 1 is a pair of biopsy forceps, in some embodiments of the present invention the surgical instrument may be a different type of endoscopic end effector such as a flexible grasper, a dissector or scissors. In the case of the biopsy forceps embodiment, the surgical instrument 30 is used to sample tissue (not shown) of a patient during surgery or endoscopy. The instrument 30 generally comprises an elongate member, generally designated by 32, having opposite ends 34, 36. A jaw assembly, generally designated by 40, is mounted on the elongate member 32 adjacent its end 34. The jaw assembly 40 includes jaws 42 mounted for independent pivotal movement relative to each other between a closed position (FIG. 7) for grasping tissue and an open position (FIG. 6 showing a partially open position) for releasing tissue. As further shown in FIG. 1, the instrument 30 comprises an actuator assembly, generally designated by 44, including an actuator member 46 operatively connected to the jaw assembly 40 for moving the jaws 42 between the open and closed positions, and a handle assembly, generally designated by 50, operatively connected to the actuator member. Although the actuator member 46 may be made of other materials without departing from the scope of the present invention, in one embodiment the member 46 is a tube having an inner diameter of between about 0.020 inch and about 0.030 inch crimped to hold a pair of wires having outer diameters of between about 0.010 inch and about 0.012 inch. Although the tube and wires may be made of other materials without departing from the scope of the present invention, in one embodiment they are made from 304 stainless steel. Although the tube may have other dimensions without departing from the scope of the present invention, in one embodiment the tube has an overall length of between about two inches and about three inches and an outer diameter of between about 0.030 inch and about 0.040 inch.

Figure 2:
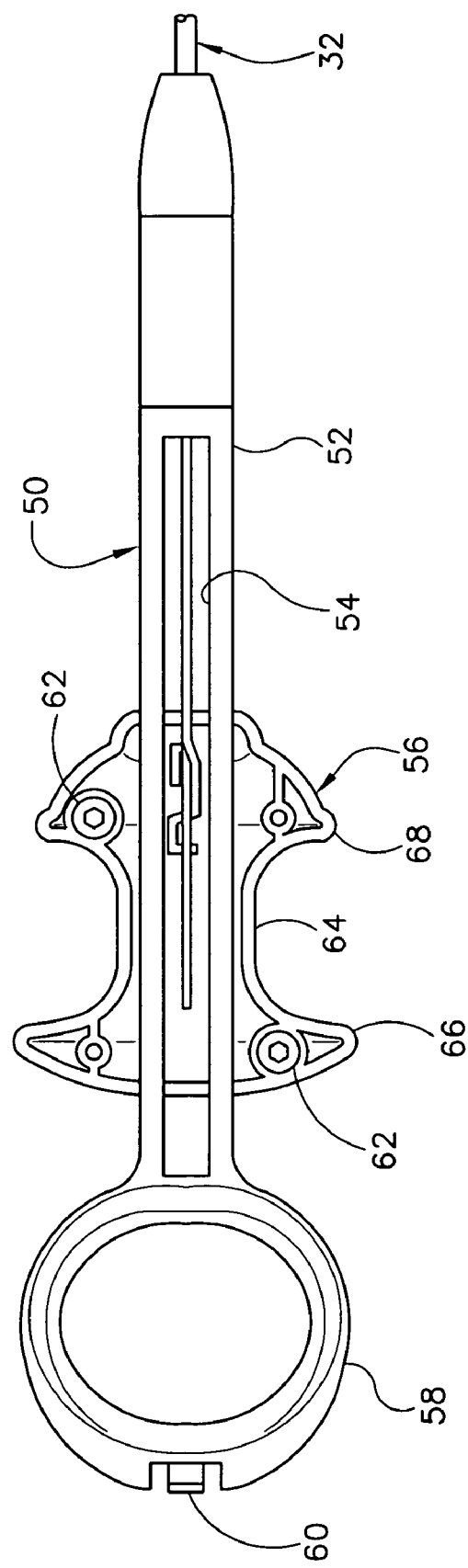
FIG. 2 is a partially disassembled side elevation of a handle assembly of the biopsy forceps.
Figure 3:
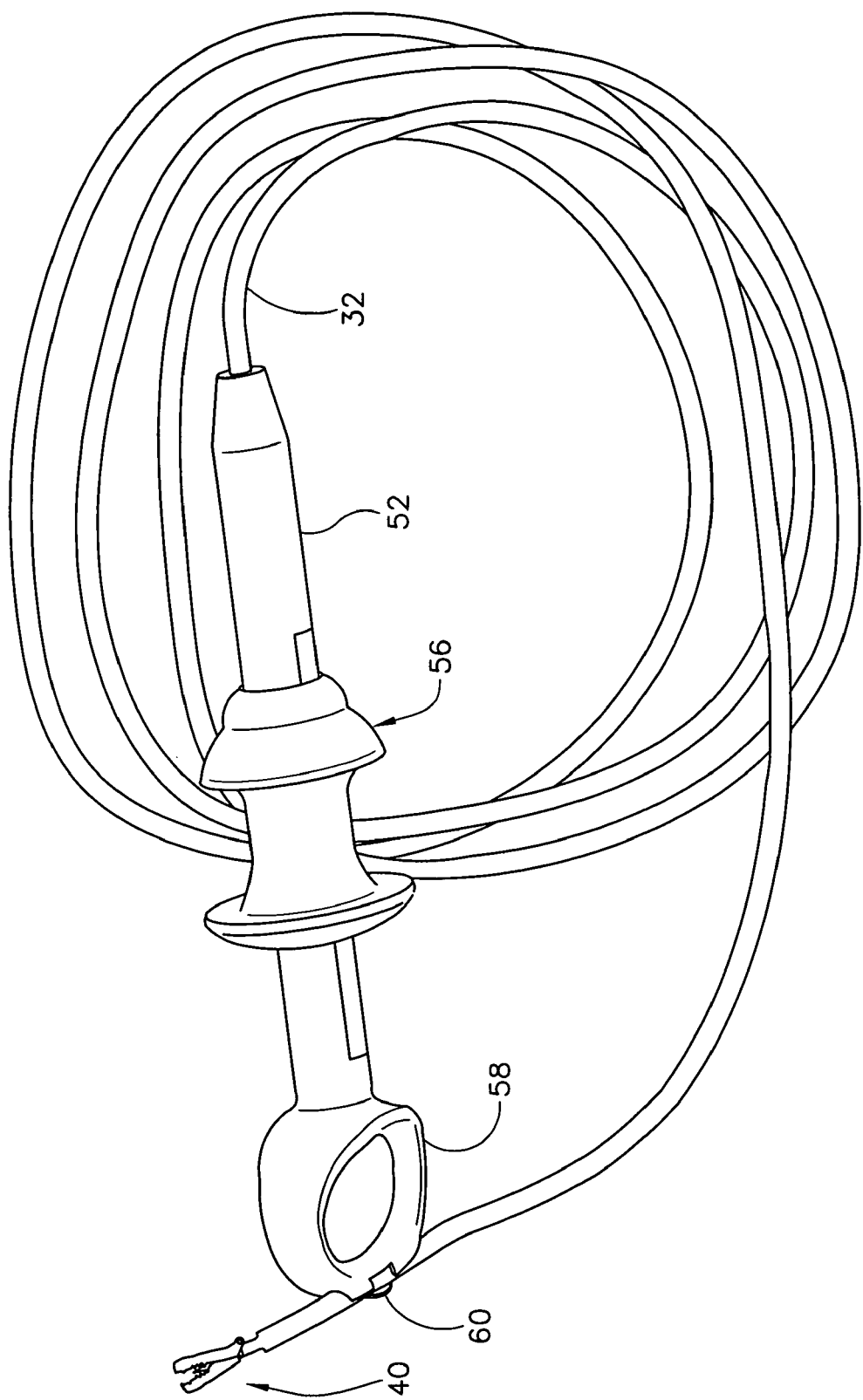
FIG. 3 is a perspective of biopsy forceps of the present invention.

As illustrated in FIG. 2, the handle assembly 50 includes a hollow shank 52 having an elongate slot 54 extending partially along its length. A spool, generally designated by 56, is slidably mounted on the shank 52 and a thumb ring 58 is provided at an end of the shank opposite the elongate member 32 for receiving a surgeon's thumb during use. A C-clip fastener 60 is provided on the thumb ring 58 for releasably connecting the elongate member 32 to the handle assembly 50 during storage and packaging as illustrated in FIG. 3. Although other fastener types may be used without departing from the scope of the present invention, in one embodiment the fastener is a C-clip integrally molded on a proximal end of the thumb ring. The spool 56 is formed in two halves joined by press pins 62 as shown in FIG. 2. In one particular embodiment, each press pin 62 has a circular cross section and is positioned in a hexagonal hole. In an alternative embodiment, the spool 56 is held together with adhesives, with screws or with detent fasteners. When assembled, the spool 56 includes an annular groove 64 formed between circumferentially extending ribs 66, 68. In use, the surgeon holds the spool 56 between his/her index finger and middle finger so that the fingers are positioned in the annular groove 64. The surgeon's thumb is inserted in the thumb ring 58. The spool 56 may be moved toward and away from the thumb ring 58 by pulling or pushing the fingers against the ribs 66, 68, respectively. Although the shank 52 and spool 56 may be made from other materials without departing from the scope of the present invention, in one embodiment the shank and spool are made from a polymer such as polycarbonate, polypropylene or ABS.

Figure 4:
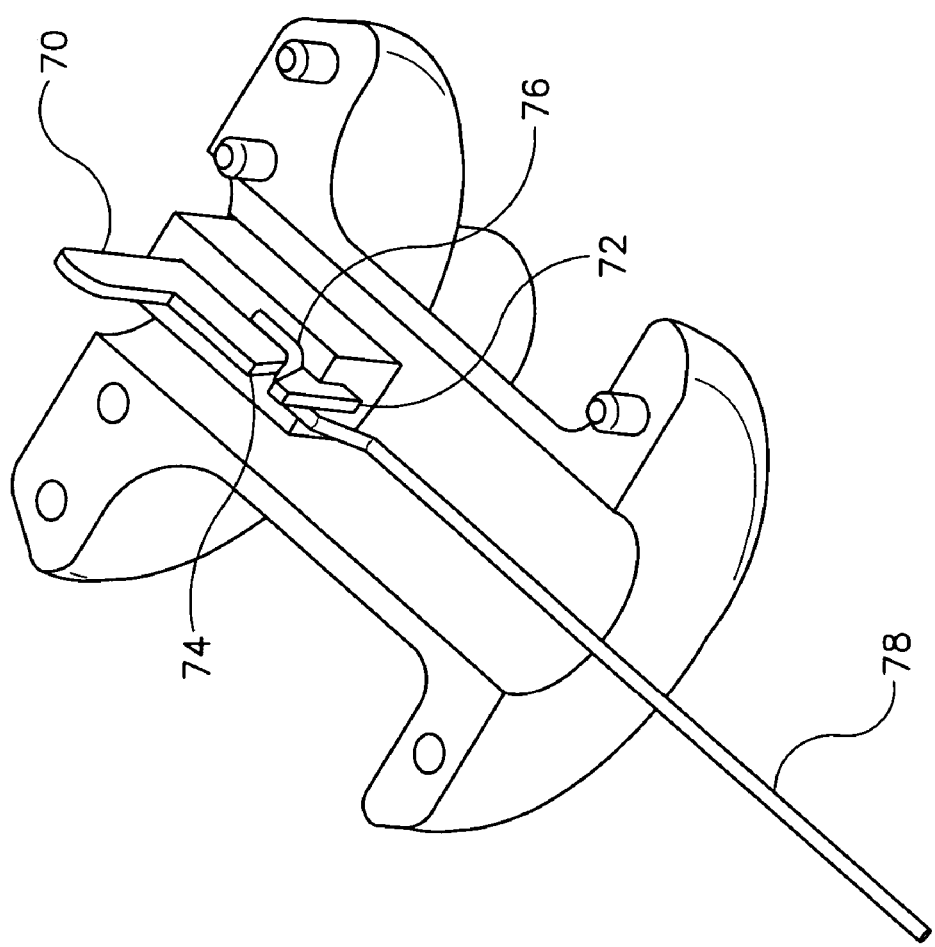
FIG. 4 is a perspective of a portion of the handle assembly of the biopsy forceps.

As illustrated in FIG. 4, a retainer 70 is captured in a recess 72 formed in the spool 56 halves. The retainer 70 includes a slot 74 for receiving a bent end 76 of the tube portion of the actuator member 46. The tubing 78 reinforces the actuator member 46. Thus, as the spool 56 is moved back and forth relative to the shank 52, the actuator member 46 slides back and forth in the elongate member 32 of the instrument 30. Although the retainer 70 may be made of other materials without departing from the scope of the present invention, in one embodiment the retainer is made of 400 series stainless steel.

Figure 5:
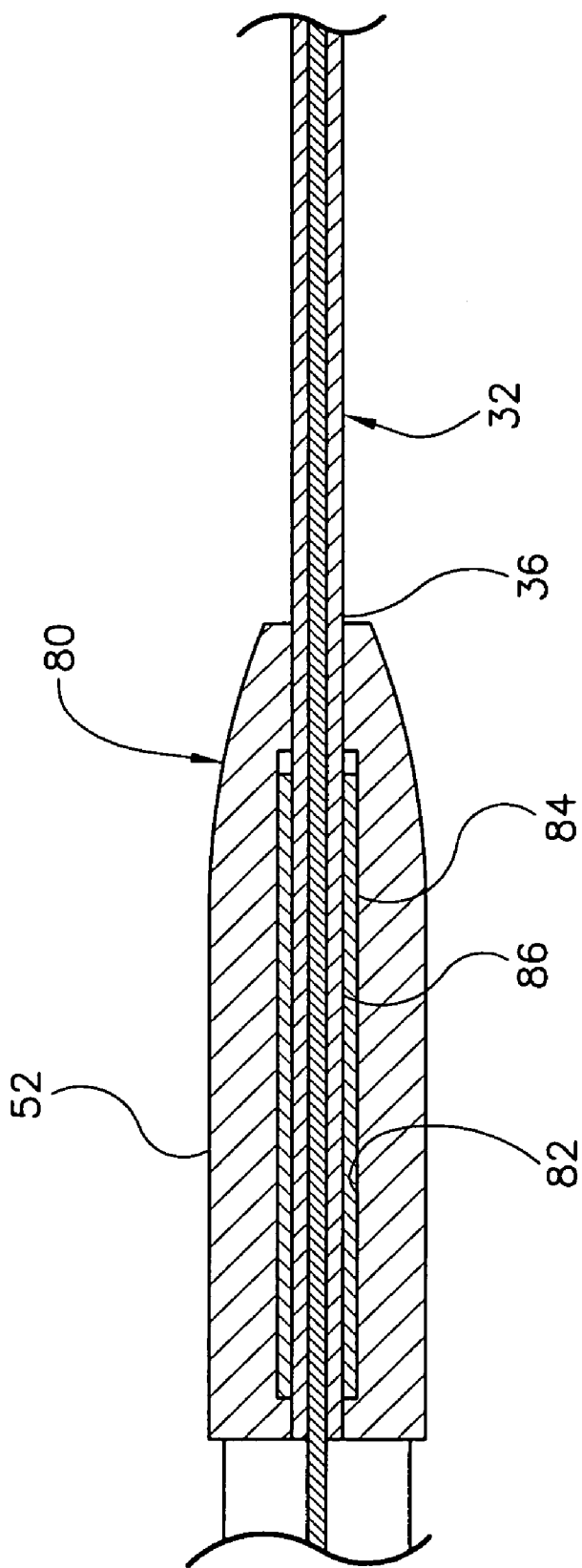
FIG. 5 is a detail in partial section of the handle assembly of the biopsy forceps.

As illustrated in FIG. 5, the shank 52 of the handle assembly 50 includes a connector portion, generally designated by 80. The connector portion 80 includes a bore 82. During assembly, the end 36 of the elongate member 32 is inserted in the bore 82. A ferrule 84 is crimped around the elongate member 32. The ferrule 84 includes barbs (not shown) that prevent the member from being withdrawn from the bore 82. Accordingly, the elongate member 32 is firmly connected to the handle assembly 50 so they form an inseparable assembly. Although the ferrule 84 may be made of other materials without departing from the scope of the present invention, in one embodiment the ferrule is made of brass. Further, although the ferrule 84 may have other dimensions without departing from the scope of the present invention, in one embodiment the ferrule has an overall length of between about 0.75 inch and about 1.25 inches, an undeformed inner diameter of between about 0.075 inch and about 0.095 inch, and an undeformed outer diameter of between about 0.100 inch and about 0.150 inch.

As shown in FIG. 6, the elongate member 32 comprises a coil 90 having an outer cover 92 and a inner lumen 94. Although the coil 90 may be made of other materials, in one embodiment the coil is made from 302 stainless steel. Although the coil may have other maximum outer diameters without departing from the scope of the present invention, in one embodiment the coil has a maximum outer diameter of between about 0.070 inch and about 0.080 inch. In one particular embodiment, the coil has a maximum outer diameter of about 0.074 inch. Although the coil 90 may have other configurations without departing from the scope of the present invention, in one embodiment the coil has a generally circular cross section and a generally uniform outer diameter. So the coil 90 has sufficient stiffness, the coil may be made so it has compressive preload. Although the coil 90 may have other compressive preloads without departing from the scope of the present invention, in one embodiment the coil has a compressive preload of between 0.75 pound and about 1.5 pounds. In other words, a tensile load of between about 0.75 pound and about 1.5 pounds is required to separate windings of the coil 90. In one particular embodiment, the coil 90 has a compressive preload of about 1.3 pounds.

Likewise, although the outer cover 92 may be made of other materials without departing from the scope of the present invention, in one embodiment the outer cover is made from polyolefin. Although the inner lumen 94 may be made of other materials without departing from the scope of the present invention, in one embodiment the inner lumen is made from high density polyethylene. Although the coil 90 may have other dimensions without departing from the scope of the present invention, in one embodiment the coil has an overall length of between about 220 centimeters and about 260 centimeters, an outer diameter of between about 0.070 inch and about 0.080 inch, and an inner diameter of between about 0.035 inch and about 0.040 inch. The coil 90 is made from wire stock having a diameter of between about 0.015 inch and about 0.020 inch. Further, although the outer cover 92 may have other outer diameters without departing from the scope of the present invention, in one embodiment the outer cover has an outer diameter of between about 0.085 inch and about 0.92 inch. Although the inner lumen 94 may have other inner diameters without departing from the scope of the present invention, in one embodiment the inner lumen has an inner diameter of between about 0.020 inch and about 0.035 inch. As the elongate member 32 is generally conventional, it will not be described in further detail.

Figure 7:
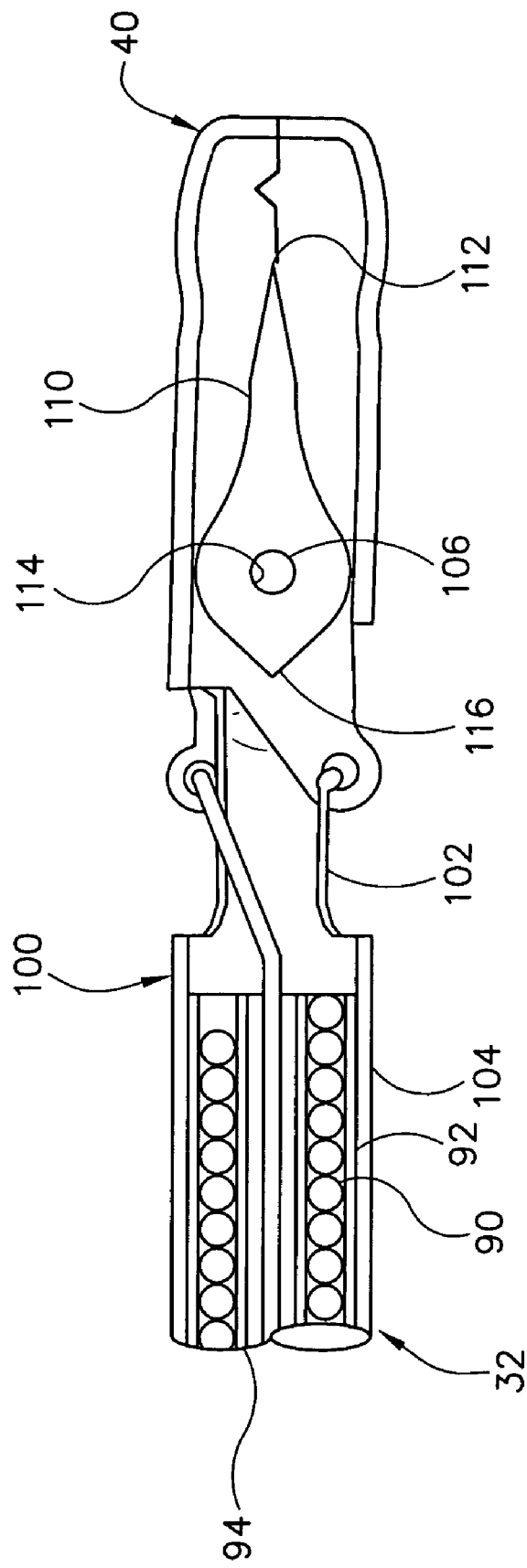
FIG. 7 is a cross section of the jaw assembly showing jaws in a closed position.
Figure 8:
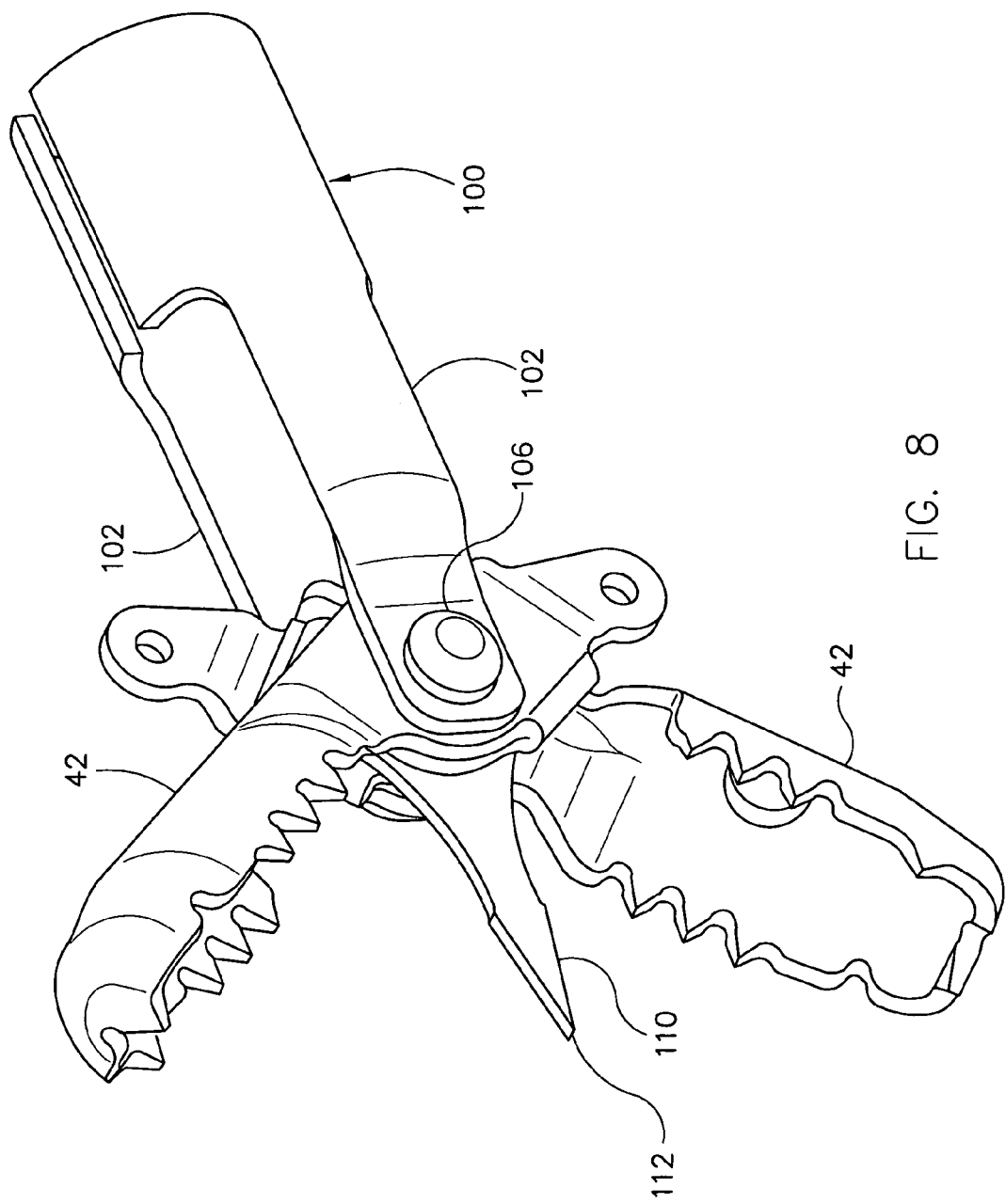
FIG. 8 is a perspective of the jaw assembly of the biopsy forceps showing jaws in an open position.

As further illustrated in FIG. 6 as well as in FIG. 7, the jaw assembly 40 includes a clevis, generally designated by 100, mounted on the end 34 of the elongate member 32. As shown in FIG. 8, the clevis includes two arms 102 extending generally parallel to each other from a barrel 104. Each of the arms 102 includes a pivot hole for receiving an axle pin 106 therein so that the axle pin extends between the arms. The axle pin 106 pivotally connects the jaws 42 of the jaw assembly 40 to the clevis 100. In addition, the axle pin 106 may connect a central needle 110 to the clevis 100. The needle 110 includes a sharp point 112 for penetrating tissue (not shown). As shown in FIG. 6, the needle 110 also includes an opening 114 for receiving the axle pin 106. The needle 110 also includes a lobe 116 opposite the point 112 for engaging the jaws 42 to hold the needle in a centered position between the jaws as will be explained in further detail below. Although the clevis 100 may be made of other materials without departing from the scope of the present invention, in one embodiment the clevis is made from 17-7 PH stainless steel. Although the axle pin 106 may be made of other materials without departing from the scope of the present invention, in one embodiment the axle pin is made from 304 stainless steel. Although the needle 110 may be made of other materials without departing from the scope of the present invention, in one embodiment the needle is made from 302 stainless steel.

Using one assembly method, the clevis 100 is positioned in a fixture (not shown). The jaws 42 and the needle 110 are positioned between the arms 102 of the clevis 100 and the axle pin 106 is inserted through the holes in the clevis, jaws and needle. The axle pin 106 is biased toward one side of the holes in the clevis 100 and joined to the clevis using a conventional method such as welding, swaging or riveting.

Figure 9:
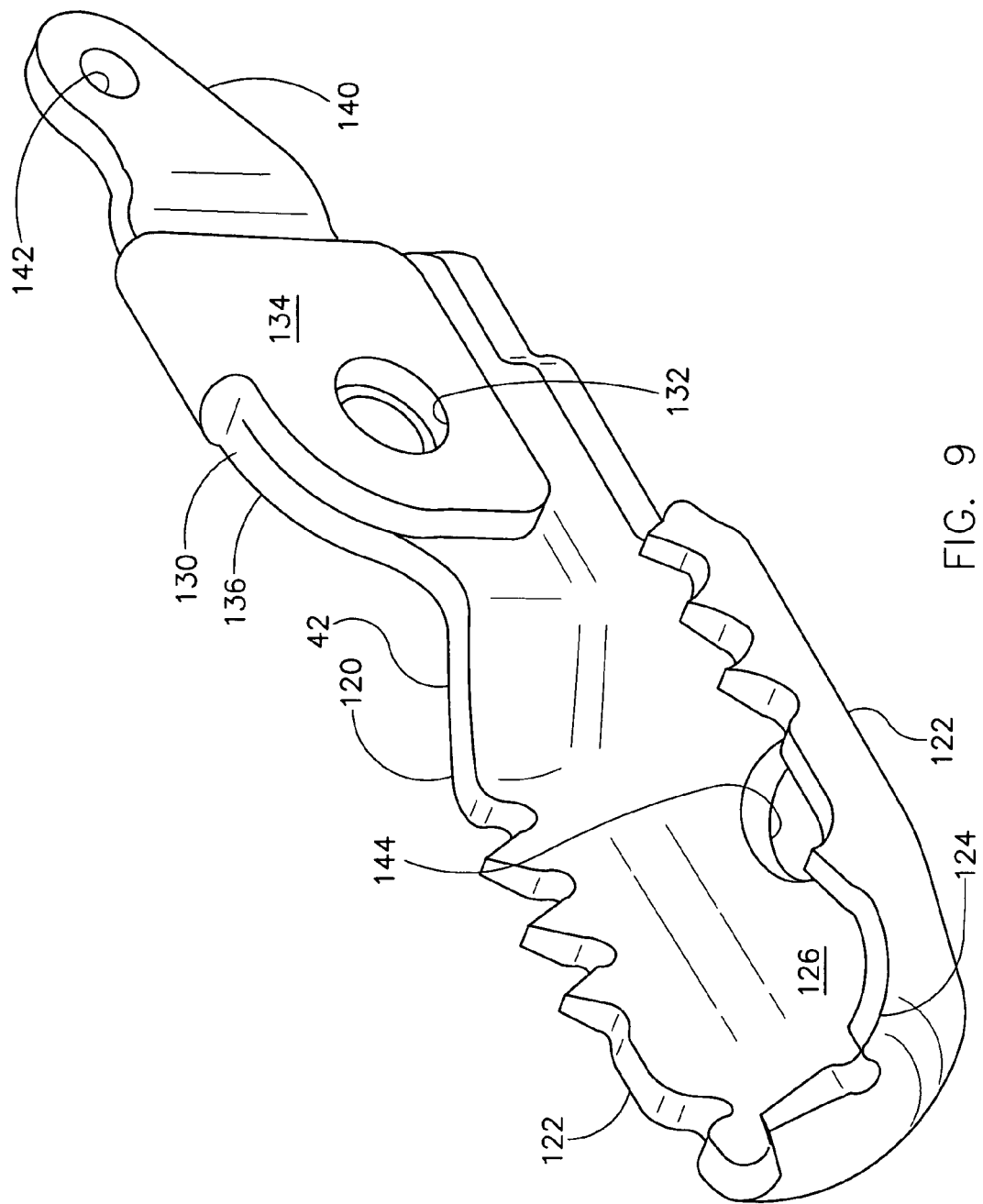
FIG. 9 is a perspective of a jaw of the jaw assembly.

As illustrated in FIG. 9, each of the jaws 42 includes a cup 120 having opposite side walls 122 extending longitudinally along the respective jaw and an end wall 124 extending across corresponding forward ends of the side walls. In one embodiment, the side walls 122 and end wall 124 extend generally perpendicular to a central land 126 of the cup 120. In addition, each jaw 42 includes a hinge extension 130 extending from one of the side walls 122. Although the jaw 42 may have other configurations without departing from the scope of the present invention, in one embodiment the other side wall 122 opposite that having the hinge extension 130 is substantially free of extensions. The hinge extension 130 extends to a pivot hole or opening 132 adapted for receiving the axle pin 106 extending between the arms 102 of the clevis 100. Although the jaws 42 may have differing configurations without departing from the scope of the present invention, in one embodiment both jaws 42 are identical to reduce manufacturing costs. In one embodiment, the hinge extension 130 includes an inner face 134 surrounding the opening 132. Further, in one embodiment with the central needle 110, the inner face 134 is offset from an imaginary median plane of the jaws 42 by a distance equal to half a thickness of the central needle. In an alternate embodiment (not shown) that does not include a central needle, the inner face is positioned on the imaginary median plane of the jaws.

The jaw 42 also includes an outer face 136 positioned to abut the clevis 100 when assembled in the biopsy forceps 30. The side walls 122 have a common tooth profile and the end 124 wall has a tooth profile different from the side wall tooth profile. Although the jaw 42 maybe formed in other ways, in one embodiment, each jaw is stamped from sheet metal and formed to shape. Although the jaws 42 may be made of other materials without departing from the scope of the present invention, in one embodiment the jaws are made from 17-7 PH stainless steel. In one particular embodiment, the hinge extension 130 includes a folded portion forming the inner face 134 extending along the median plane and the outer face 136 positioned to abut the clevis 100 when assembled in the biopsy forceps 30. Although hinge extension 130 may be folded in other ways without departing from the scope of the present invention, in one embodiment the extension is folded along a substantially straight fold extending parallel to a longitudinal axis of the jaw. Each jaw 42 also includes a control arm 140 for pivoting the respective jaw about the axle pin 106. Although the control arm 140 may have other configurations, in one embodiment the control arm is integrally formed as part of the hinge extension 130. The control arm 140 includes an actuation hole or opening 142 for receiving the actuator member 46. In one embodiment, each cup 120 includes an opening 144 allowing the respective cup to drain.

Figure 10:
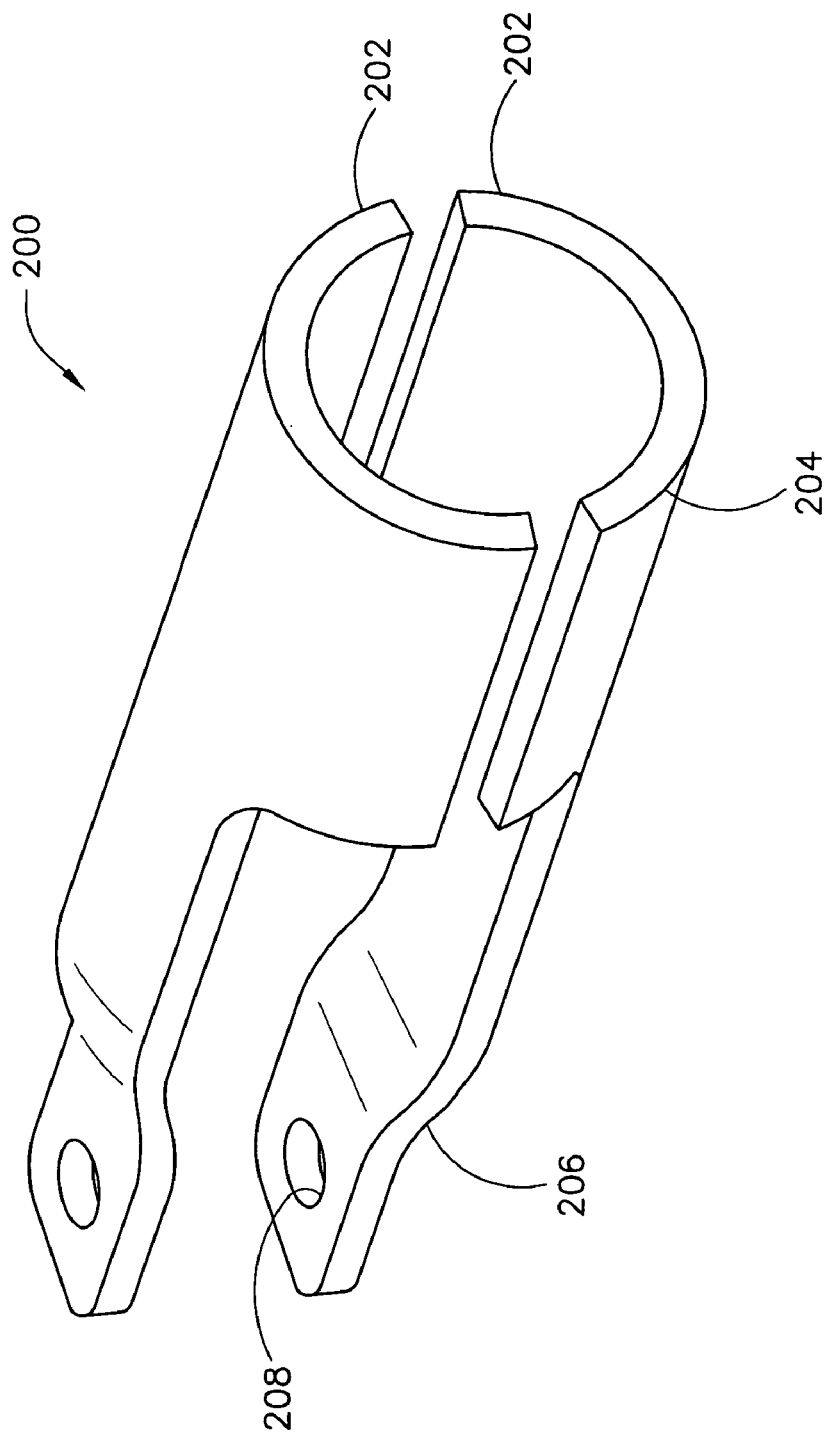
FIG. 10 is a perspective of a first alternative clevis.

An alternative embodiment of the clevis is generally designated by the reference number 200 in FIG. 10. The clevis 200 is formed in two pieces 202. Each piece includes a barrel portion 204 for engaging the end 34 of the elongate member 32. Each clevis half 202 further includes an arm 206. Each arm 206 includes a hole 208 for receiving the axle pin 106 therein. To assemble the jaw assembly 40 using the alternate clevis embodiment shown in FIG. 10, one of the clevis halves 202 is joined to an axle pin 106 to form a master clevis piece. The master clevis piece is held in position against the end 34 of the elongate member 32 and the jaws 42 and needle 110 are mounted on the axle pin 106. The second half of the clevis 202 is placed over the first half and the axle pin 106 is laser welded to the corresponding hole 208 in the clevis arm 206. The barrels 204 of the clevis halves 202 are simultaneously welded (e.g., laser welded) to the end 32 of the elongate member 32. It is envisioned that this assembly method would simplify the assembly process even when additional components (not shown) such as spacers and spring washers are added to the assembly. Because the clevis 200 is split, component tolerances may be larger. As other features of the clevis 200 are identical to those described above, they will not be described in further detail.

Figure 11:
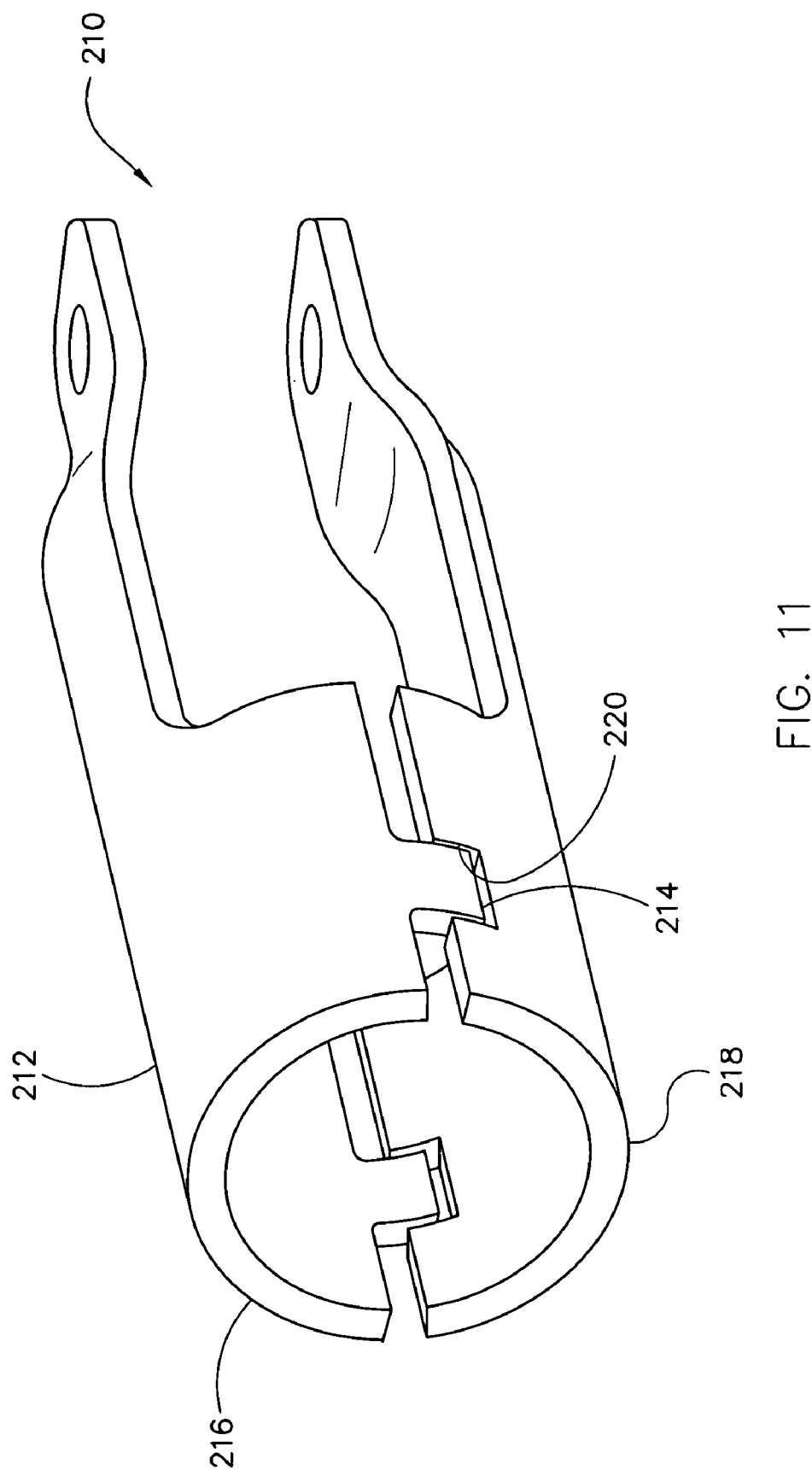
FIG. 11 is a perspective of a second alternative clevis.

FIG. 11 shows a second alternative embodiment of a clevis generally designated by the referenced number 210. This embodiment of the clevis 210 is identical to the first alternative embodiment of the clevis 200 described above except that one clevis half 212 includes protrusions such as rectangular tabs 214 extending from its barrel 216. The barrel 218 of the other half includes recesses such as rectangular notches 220 for accommodating the tabs 214. This second alternative embodiment allows for one clevis half to extend more than half way around the end 34 of the elongate member 32 to aid in holding the clevis half in place during assembly. The tabs 214 and notches 220 also constitute alignment features that aid in locating the second clevis half. In a variation on this alternative embodiment, a notch or other locating feature may be included on the barrel of the clevis 210 for aligning the clevis with the end 34 of the elongate member 32. Because other features of the clevis 210 are identical to those described above, they will not be described in further detail.

Both of the devises described above are assembled using a similar method. A first clevis half is positioned in a fixture (not shown). The jaws are positioned on the first clevis half and if a central needle is used it is positioned between the jaws. A second clevis half is positioned on the jaw assembly. The stacked components are squeezed together by the fixture and then the fixture is relaxed so that a total accumulated stack gap between the components is within a tolerance selected to assure proper operation of the jaws. Although other accumulated gaps may be used without departing from the scope of the present invention, in one embodiment the accumulated gap is between about 0.0005 inch and about 0.003 inch. After the stack gap is adjusted, a pivot member or pivot pin is inserted through the components and fastened in place. The actuator member may be connected to the jaws at a convenient time during the assembly.

Figure 12:
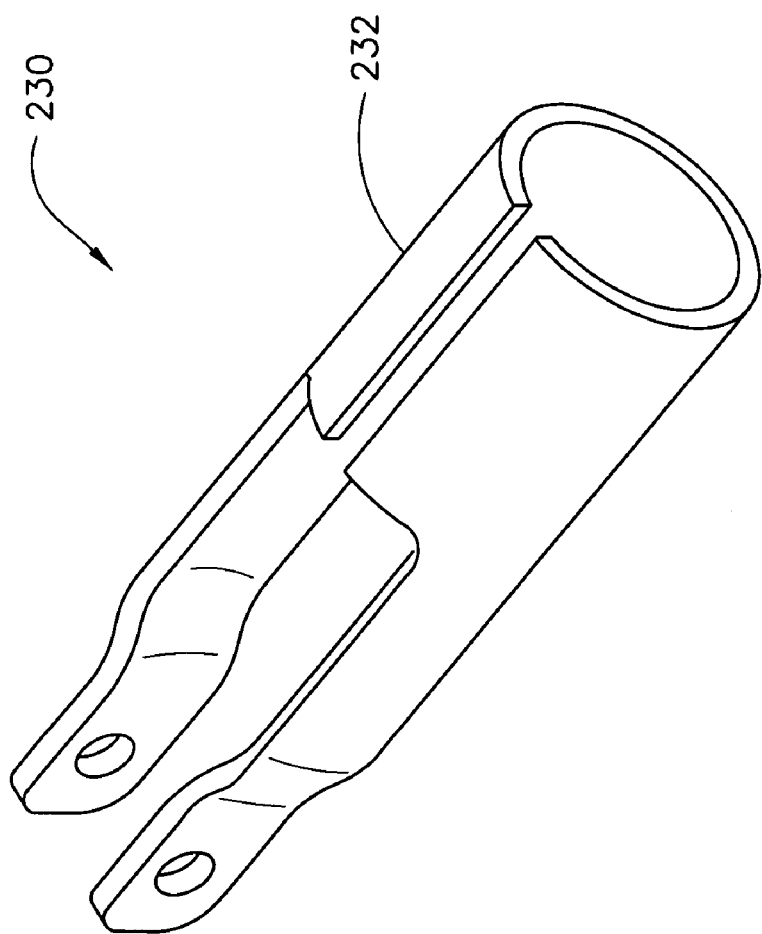
FIG. 12 is a perspective of a third alternative clevis.

A third alternative embodiment is generally designated by the reference number 230 in FIG. 12. This third alternative embodiment of the clevis 230 is identical to the first alternative embodiment 200 illustrated in FIG. 10 except that the clevis halves are joined on one side, leaving a slot 232 along one side. In one embodiment of the third alternative clevis 230, the jaw assembly 42 is assembled without assembling the clevis 230 to the end 34 of the elongate member 32. This jaw assembly 42 may be manufactured remote from the overall instrument. The slot 232 has an advantage of aiding in inserting the actuation member 46 during assembly. Other features of the clevis 230 are identical to those described above and will not be described in further detail.

Figure 13:
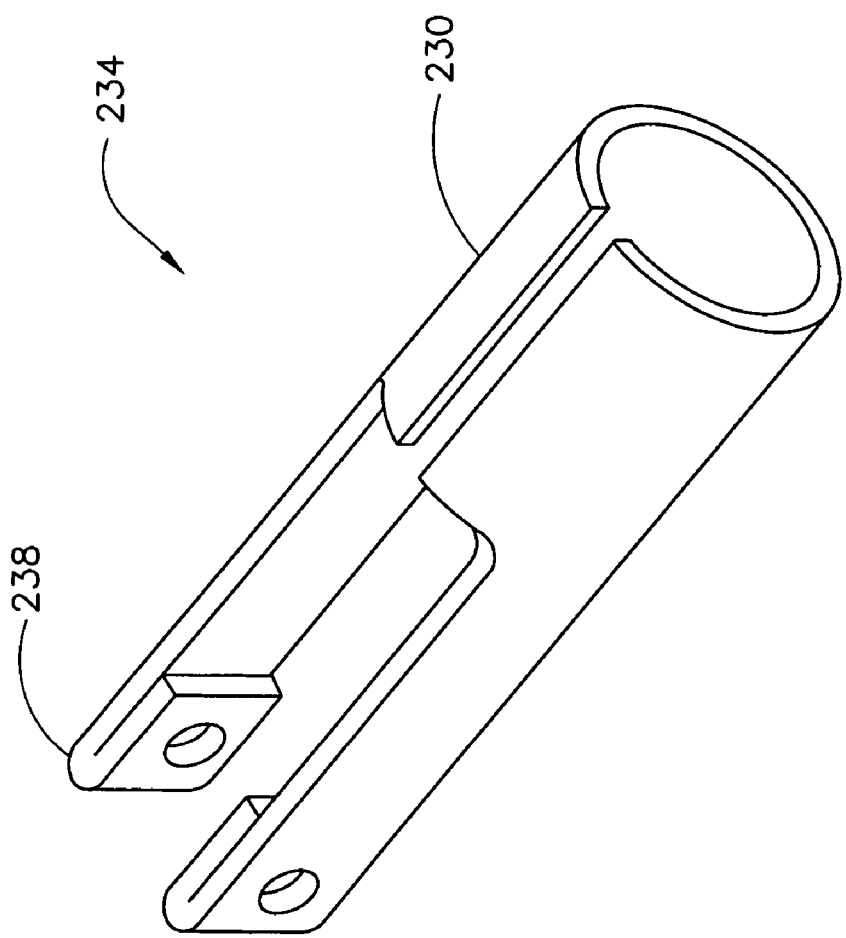
FIG. 13 is a perspective of a fourth alternative clevis

FIG. 13 illustrates a fourth alternative embodiment generally designated by the reference number 234. The fourth alternative embodiment of the clevis 234 is identical to the third alternative embodiment 230 except that the clevis includes arms 236 having folded portion 238. Other features of the clevis 234 are identical to those described above and will not be described in further detail.

The devises described above having joined halves are assembled similarly to the previously described method except that the first and second clevis halves are simultaneously positioned on the fixture and the jaws and needle are inserted between the arms of the clevis during assembly rather than stacked in sequence. Other aspects of the assembly method are identical and will not be described in further detail.

Figure 14:
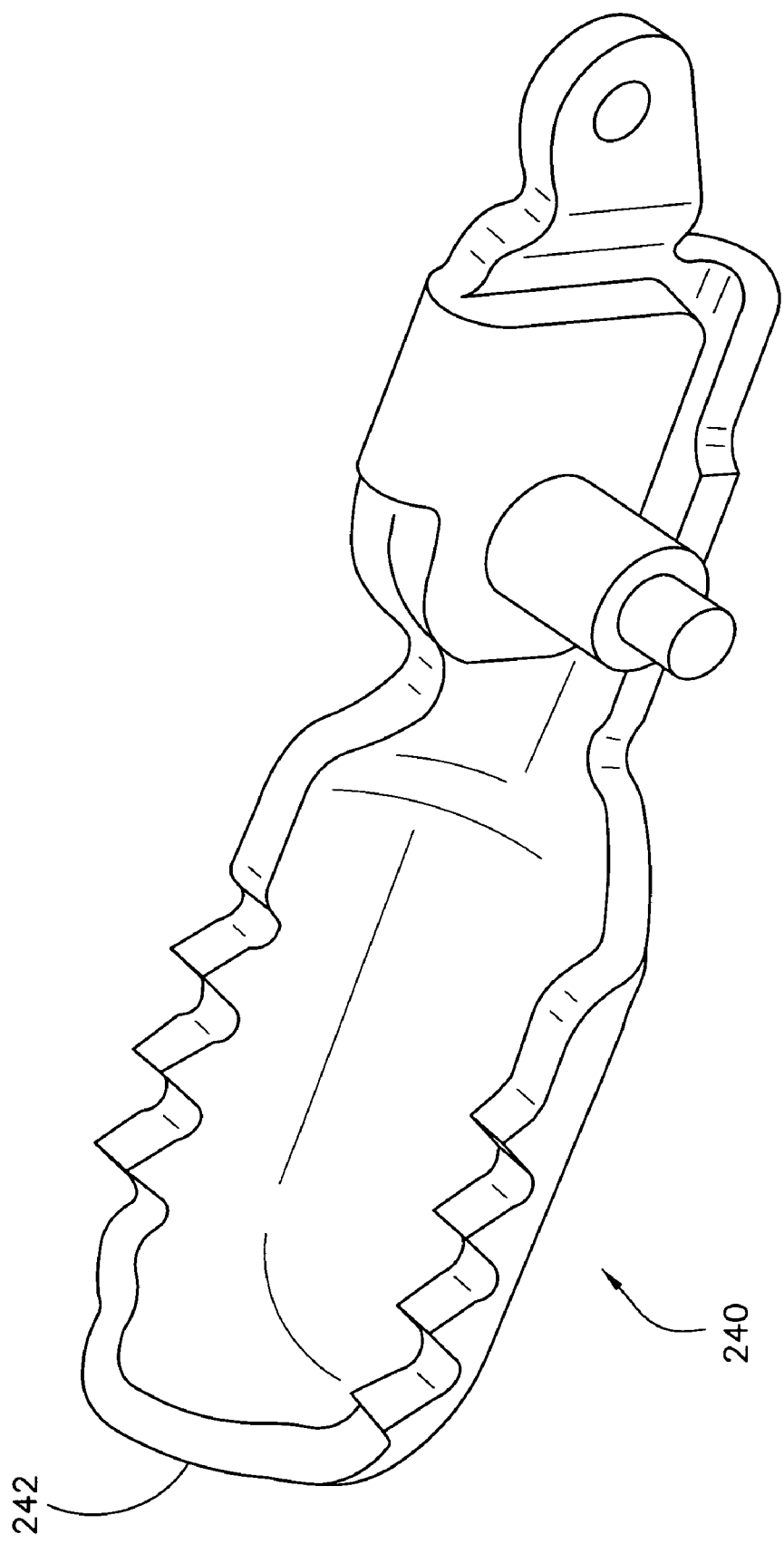
FIG. 14 is a perspective of a first alternative jaw.
Figure 15:
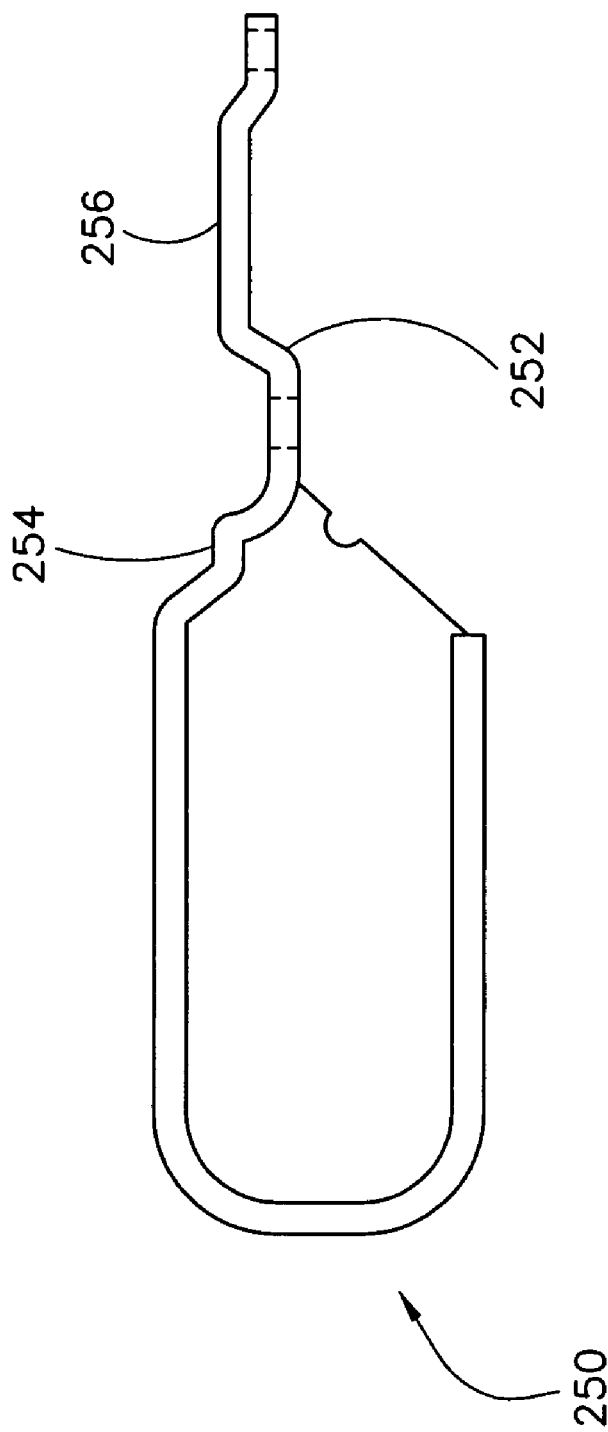
FIG. 15 is a top plan of a second alternative jaw.

FIG. 14 illustrates an alternative embodiment of a jaw 240. The jaw 240 is identical to the previously discussed jaw 42 except that the end wall 242 has a sinusoidal tooth profile and the drain hole 144 is omitted. The side walls 122 (FIG. 9) of this embodiment have a tooth profile that is generally uniform and repeating. For example, the side wall tooth profile has generally saw tooth shape. Further, as will be appreciated by examining FIG. 14, the spacing of tooth profile of the end wall 242 is longer than that of the tooth profile of the side walls 122. FIG. 15 discloses a second alternative embodiment of the jaws, generally designated 250. The second alternative embodiment of the jaw 250 is similar to the first embodiment of the jaw 42 described above except that the folded portion of the hinge extension 130 is replaced with an embossed portion 252. This embossed portion 252 is positioned longitudinally between two other portions 254, 256. The embossed portion 252 includes an inner face extending along the median plane. The other portions 254, 256 include the outer face positioned to abut the clevis 100 when assembled in the biopsy forceps 30. Because other features of the jaws are identical to those described above, they will not be described in further detail.

Figure 16A:
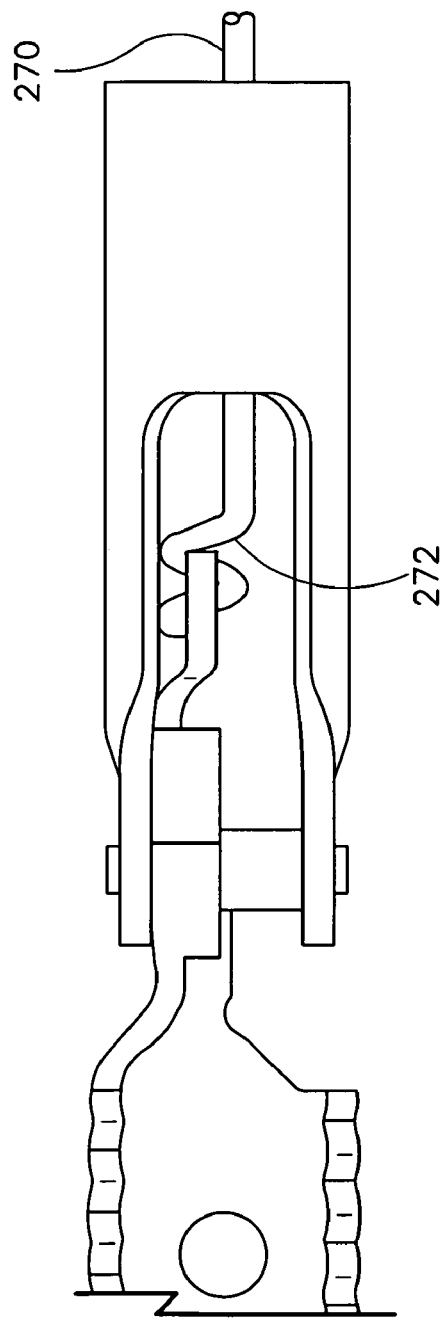
FIGS. 16A and 16B are top plans of first and second alternative actuator members, respectively.
Figure 16B:
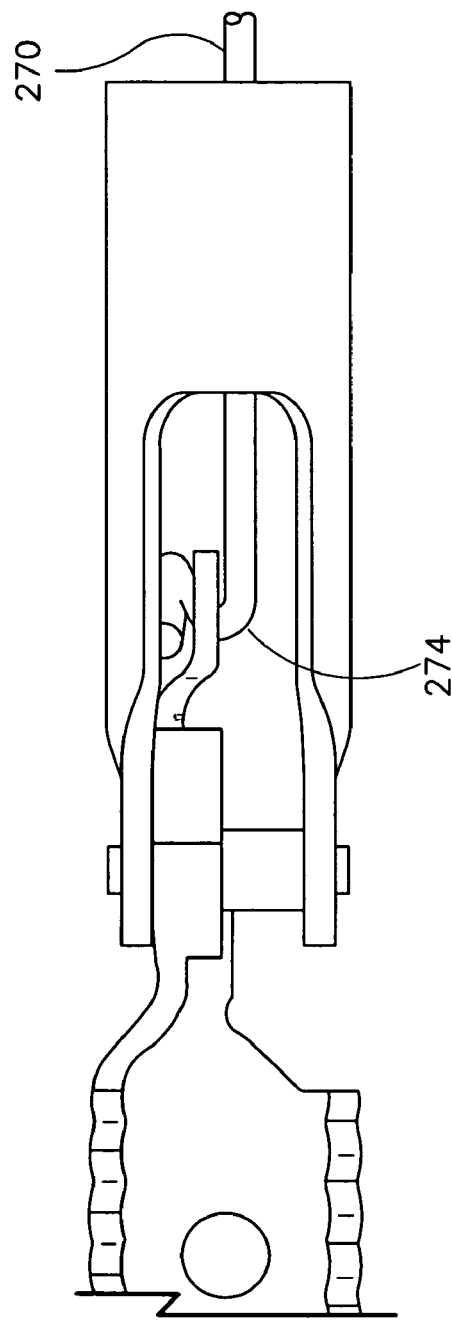
Figure 17:
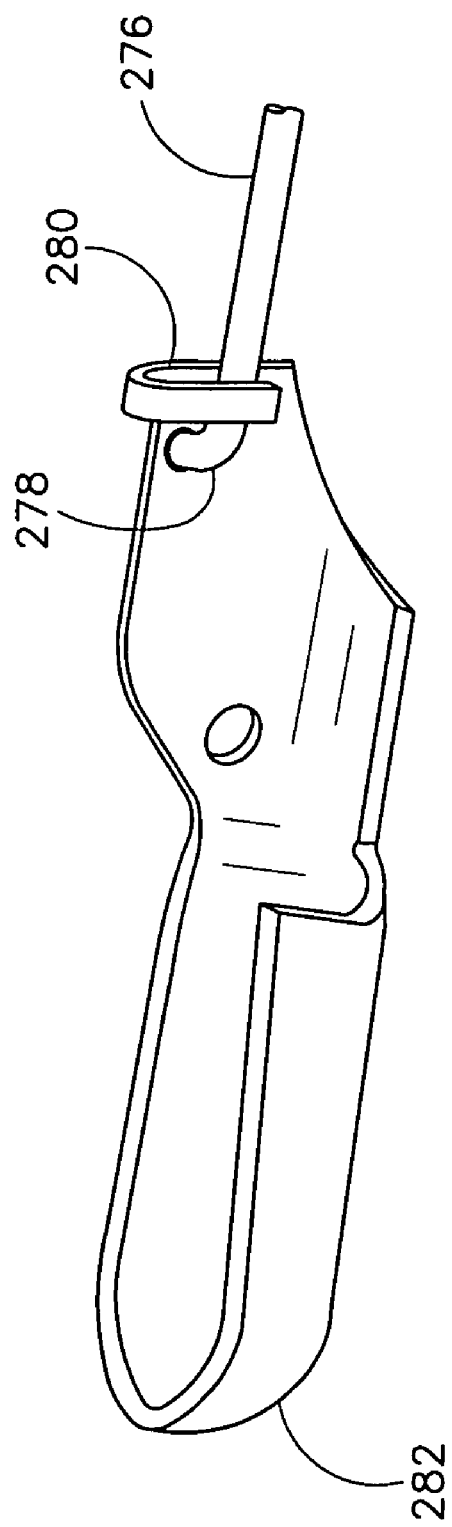
FIG. 17 is a perspective of a second alternative actuator member and jaw.

FIG. 16A illustrates a partial jaw assembly and an alternative embodiment of an actuator member 270. The actuator member 270 comprises an actuator wire having a helical portion 272 for connecting the actuator member to the control arm 140 of the jaw 42. The helical portion 272 of the actuation wire 270 permits the wire to be easily threaded into the opening 142 in the control arm 140 of the jaw 42 to save assembly time and eliminate other processes for connecting the wire to the control arm (e.g., heading). FIG. 16B illustrates a partial jaw assembly and a second alternative embodiment of an actuator member 270. The actuator member 270 comprises an actuator wire having a helical portion 274 similar to that of the previously described embodiment except that the helical portion of the second alternative embodiment is wound about a lateral axis rather than a longitudinal axis. In a third alternative embodiment illustrated in FIG. 17, the actuation wire 276 includes a bent end 278. A U-shaped tang 280 formed on the jaw 282 adjacent the control arm opening 142 retains the actuation wire 276 in position in the control arm opening. To assemble the actuation wire 276 of the second alternative embodiment, the bent end 278 of the wire 276 is inserted in the opening 142 and then the jaw 282 is rotated relative to the wire so the tang 280 engages the wire to prevent removal of the bent portion of the wire from the opening. As other features of the actuator members and jaws of these embodiments are identical to those described above, they will not be described in further detail.

Figure 18:
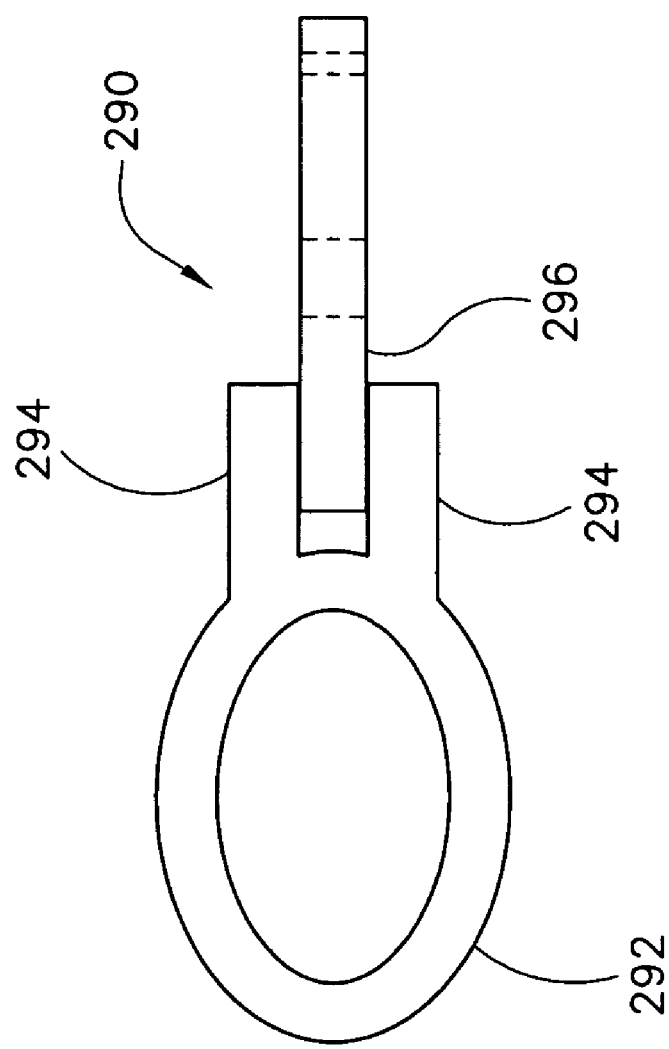
FIG. 18 is a top plan of a third alternative jaw.

FIG. 18 illustrates an alternative embodiment of a jaw, generally designated by 290. Rather than having an integral cup and hinge extension, the jaw 290 of this alternative embodiment is made from separate pieces. The jaw has a cup 292 with a pair of hinge connectors 294 extending from it for joining a hinge extension 296 to the cup. The hinge extension 296 maybe connected to the hinge connector 294 by any suitable means such as laser welding or adhesives. As will be apparent to those skilled in the art, the jaw cup 292 of the alternative embodiment has a different shape than those disclosed above. The primary difference between the jaw cup 292 shown in FIG. 18 and those previously disclosed is that the side walls are spaced farther from the median plane at a position between the front end and the back end than at the front end and at the back end. This configuration permits the end effector to travel through tighter radiuses without binding. The jaw cup of this embodiment permits a larger volume of tissue to be removed while maintaining the same minimal bend radius. Cups having other shapes are also envisioned as being within the scope of this embodiment. For example, rather than having an oval shape as shown, the cup may have an hourglass shape or a tapered shape.

Figure 19:
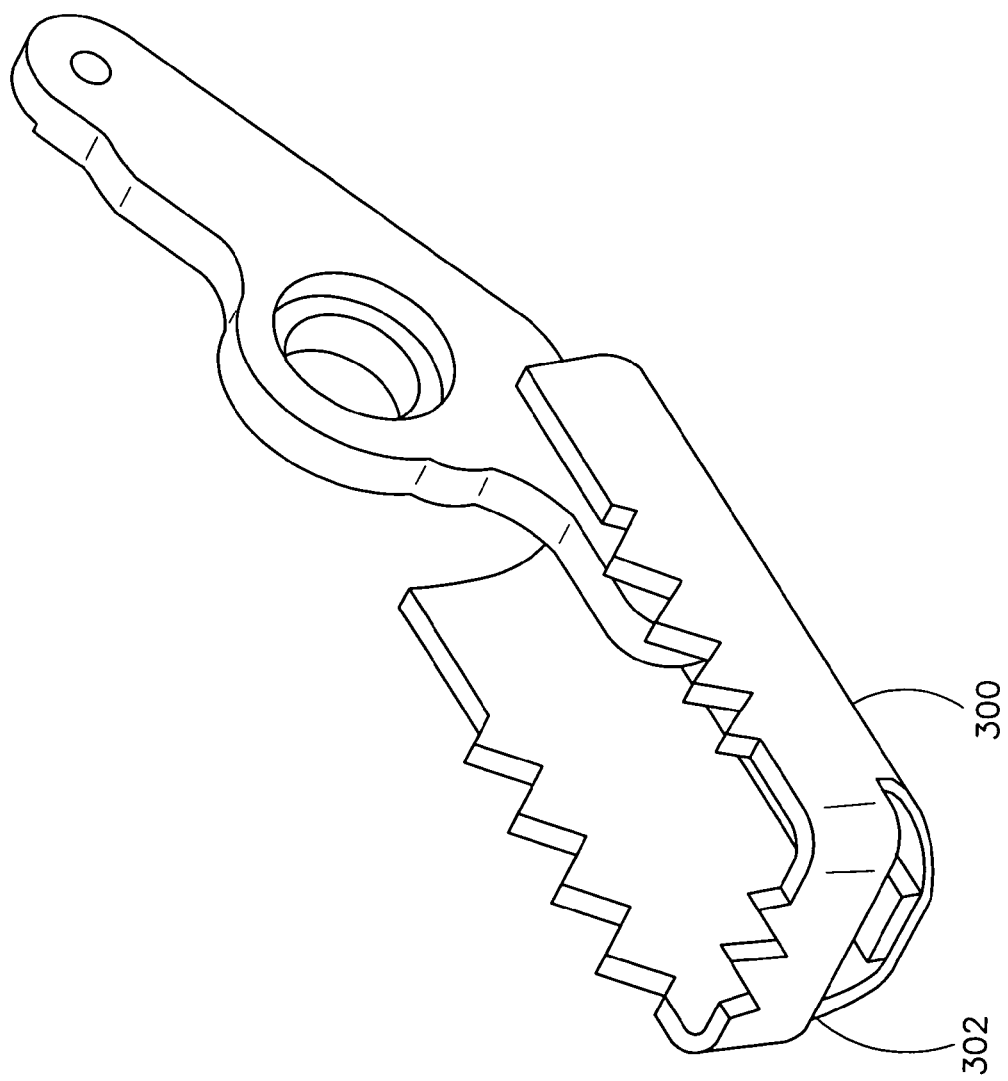
FIG. 19 is a perspective of a fourth alternative jaw.
Figure 20:
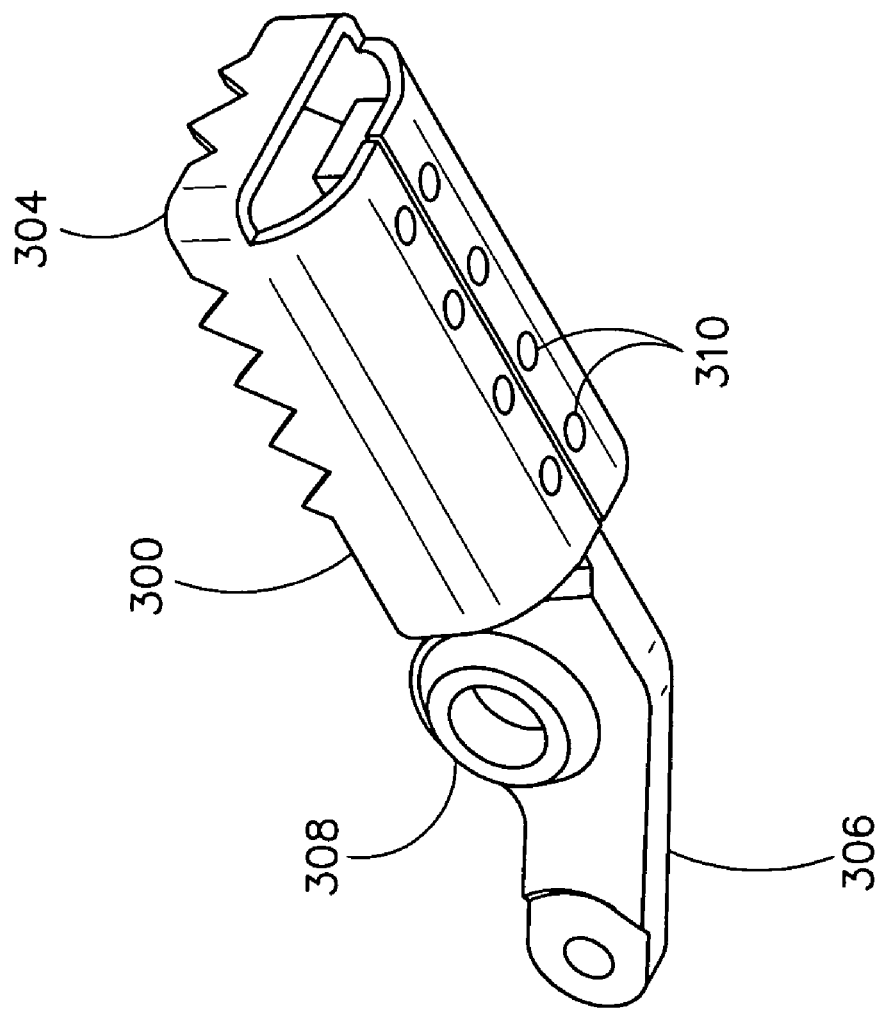
FIG. 20 is an alternate perspective of the fourth alternative jaw.

FIG. 19 illustrates a second alternative embodiment of a jaw 300 that maximizes tissue volume removed. In this embodiment, the end wall 302 has a substantially plainer portion so the cup encompasses a generally rectilinear volume. FIG. 20 illustrates an alternate view of the jaw illustrated in FIG. 19. The jaw 300 maybe formed in two pieces, a cup 304 and a hinge extension 306. The cup 304 maybe formed from sheet metal and the hinge extension 306 maybe formed of a polymer such as glass filled nylon. One benefit of this design is that the hinge extension 306 may have molded features (e.g., bushing 308) rather than a substantially constant thickness. This provides additional material where stresses are higher or where wear is likely to occur. In addition, the two piece design permits the use of different materials in different parts of the jaw 300 to optimize the design. The cup 304 and hinge extension 306 may be joined by any conventional means. For example, the cup 304 and hinge extension 306 may be joined by heating the hinge extension so that it is molded into holes 310 formed in the cup to mechanically join the components.

Figure 21A:
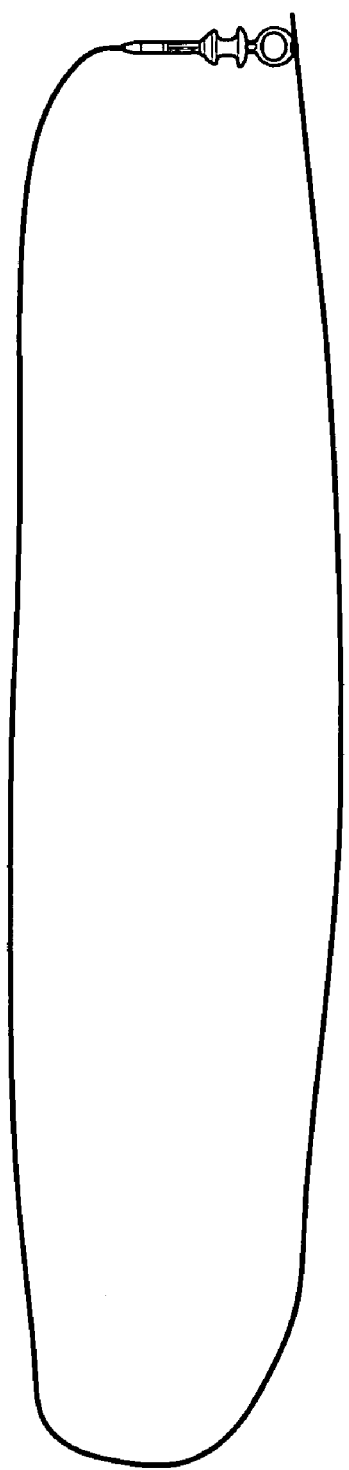
FIGS. 21A-E illustrate a sequence of movements used to prepare the instrument for packaging using one method.
Figure 21B:
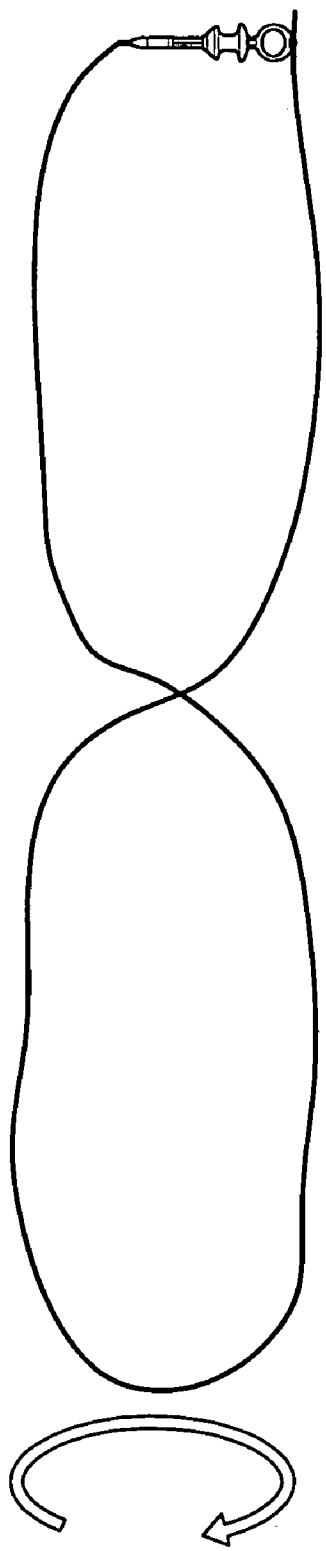
Figure 21C:
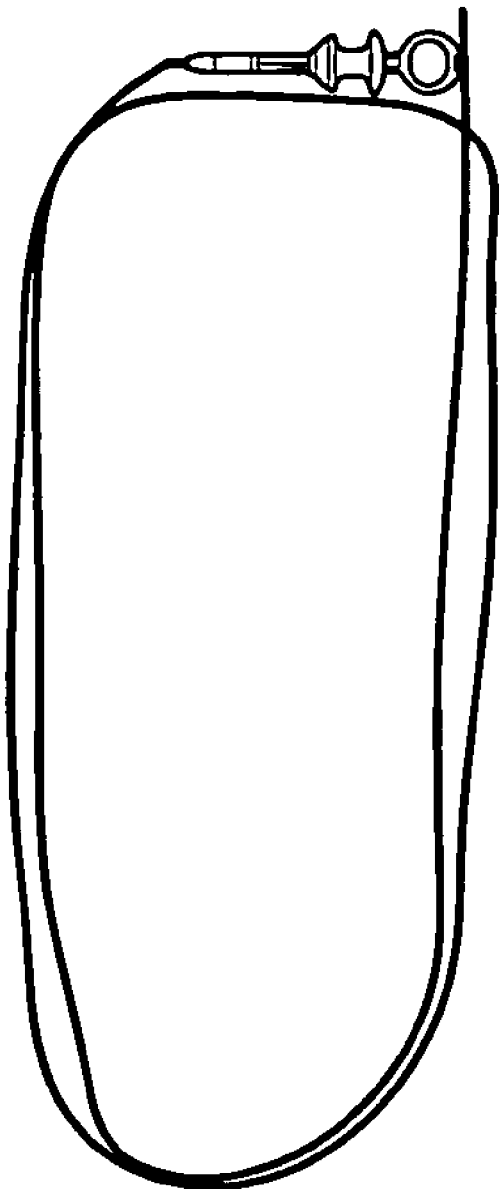
Figure 21D:
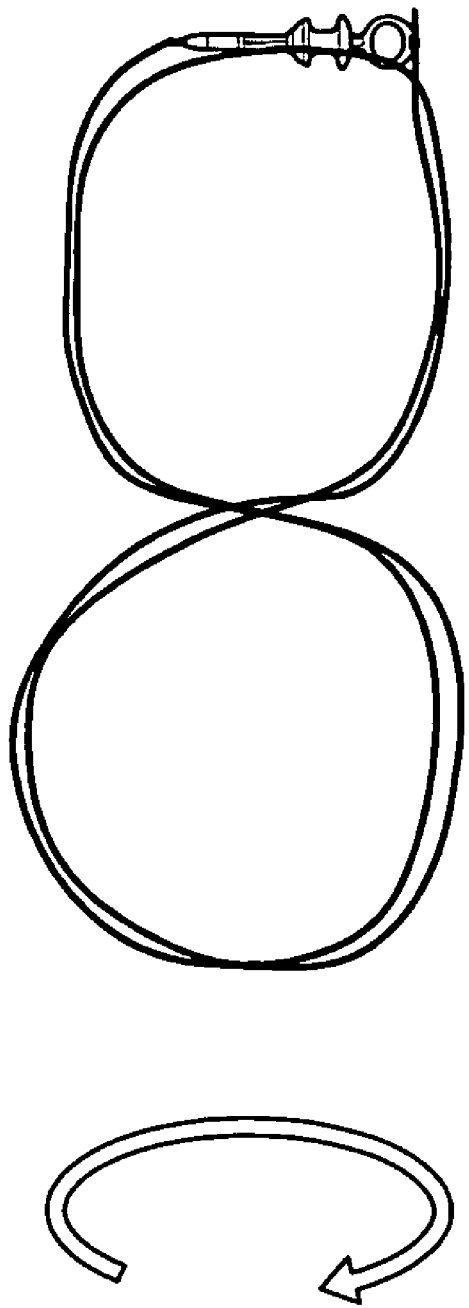
Figure 21E:
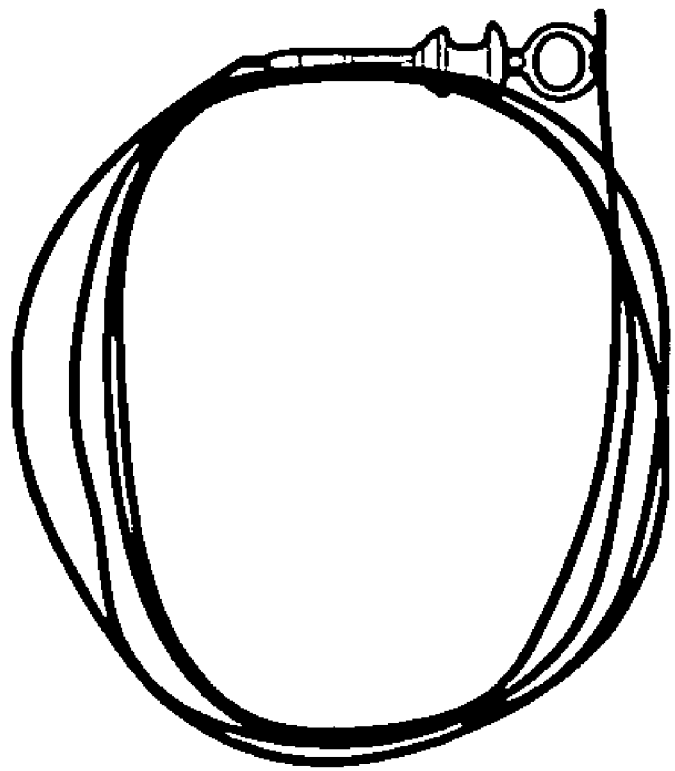

The instrument described above may be wound in a conventional manner prior to packaging. One method of preparing the instrument for packaging is particularly advantageous because it reduces the likelihood of the instrument becoming tangled and/or springing apart so it is damaged to contaminated. The effector assembly is fastened to the to the fastener on the handle to form a first loop as illustrated in FIG. 21a. The loop is grasped at opposite ends and one end is twisted relative to the other through an angle of about 180 degrees to move the loop into a figure-8 configuration as illustrated in FIG. 21b. Opposite ends of the figure-8 configuration are moved together into an overlapped loop configuration shown in FIG. 21c. The overlapping loop is grasped at opposite ends and one end is twisted relative to the other through an angle of about 180 degrees to move the loop into a double figure-8 configuration as illustrated in FIG. 21d. In one embodiment, the ends of the overlapped loop are twisted in a direction opposite to that which the loop was previously twisted as shown by the arrows in FIGS. 21b and 21d. Lastly, opposite ends of the double figure-8 configuration are folded together to move the double figure-8 configuration into a quadruple overlapped loop configuration as illustrated in FIG. 21e. The instrument in this final configuration may be packaged in a conventional sterile packaging.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An end effector for use in an endoscopic device, said end effector comprising:
   a cup; and
   a hinge extension formed separately from the cup and connected to the cup, the hinge extension having a pivot for pivotally connecting the end effector to an identical second end effector,
   the cup including a central land having opposite sides, opposite side walls extending from the opposite sides of the central land between a front end and a back end, and an end wall extending across the front ends of said opposite side walls; and
   the central land includes an integral hinge connector portion and the hinge extension is positioned in overlapping relation with the hinge connector portion and directly connected to the hinge connector portion of the cup along substantially the entire length of the central land, wherein the hinge connector portion lies in a plane which is substantially the same as a plane in which the central land lies.

2. An end effector as set forth in claim 1 wherein the hinge connector portion comprises two elements spaced by a gap and the hinge extension is positioned over the gap between the elements when connected to the hinge connector.

3. An end effector as set forth in claim 1 wherein the hinge extension comprises a material different from that of the cup.

4. An end effector as set forth in claim 3 wherein the hinge extension comprises a polymer.

5. An end effector as set forth in claim 4 wherein the hinge connector portion of the cup includes an opening and the hinge extension includes a projection extending through the opening to connect the hinge extension to the cup.

6. An end effector as set forth in claim 4 wherein the hinge connector portion of the cup includes plural holes and the hinge extension is molded into the holes to mechanically join the cup to the hinge extension.

7. An end effector as set forth in claim 1 wherein the cup has a thickness and the hinge extension has a thickness different than the cup thickness.

8. An end effector as set forth in claim 7 wherein the cup thickness is thinner than the hinge extension thickness.

9. An end effector as set forth in claim 1 wherein the hinge extension includes an integral bushing.

10. An end effector for use in an endoscopic device, said end effector comprising:
    a cup; and
    a hinge extension formed separately from the cup and connected to the cup, the hinge extension having a pivot for pivotally connecting the end effector to an identical second end effector,
    the cup including a central land having opposite sides, opposite side walls extending from the opposite sides of the central land between a front end and a back end, and an end wall extending across the front ends of said opposite side walls;
    the central land includes an integral hinge connector portion and the hinge extension is positioned in overlapping relation with the hinge connector portion and directly connected to the hinge connector portion of the cup along substantially the entire length of the central land, wherein the hinge connector portion lies in a plane which is substantially the same as a plane in which the central land lies; and
    wherein said cup has a longitudinally extending median plane and the opposite side walls extend on opposite sides of the median plane, the opposite side walls extending perpendicular to the central land of the cup, each of said opposite side walls extending between a front end and a back end, each of said opposite side walls being spaced a first distance from the median plane at a position between the front end and the back end and spaced a second distance from the median plane different from the first distance at the front end.

11. An end effector as set forth in claim 10 wherein each of said side walls is spaced farther from the median plane at a position between the front end and the back end than at the back end.

12. An end effector as set forth in claim 11 wherein each of said side walls is curved.

13. An end effector as set forth in claim 12 wherein each of said side walls includes a radius having a center of curvature, and wherein the center of curvature of the side walls are positioned on an opposite side of the median plane.

14. An end effector as set forth in claim 13 wherein the center of curvature of each side wall extends generally parallel to the median plane.

15. An end effector as set forth in claim 10 wherein said first distance is greater than said second distance.

16. An end effector as set forth in claim 10 wherein each of said opposite side walls being spaced a third distance from the median plane different from the first distance at the back end.

17. An end effector as set forth in claim 16 wherein said first distance is greater than said second distance and the third distance.

18. An end effector as set forth in claim 17 wherein said second distance is generally equal to said third distance.

* * * * *